US005502944A

United States Patent [19]
Kraft et al.

[11] Patent Number: 5,502,944
[45] Date of Patent: Apr. 2, 1996

[54] MEDICATION DISPENSER SYSTEM

[75] Inventors: Thomas L. Kraft; Lisa W. Rogers, both of Houston; Van Hoskins, Friendswood; Lou Waters; Robert Meyers, both of Houston; Kenneth E. Reynolds, Denton; Stuart S. Crader, Dallas; David Loebig, Rosenberg, all of Tex.

[73] Assignee: Owen Healthcare, Inc., Houston, Tex.

[21] Appl. No.: 161,899

[22] Filed: Dec. 3, 1993

[51] Int. Cl.⁶ ............................. B65B 57/20; G07F 7/02
[52] U.S. Cl. .............................. 53/55; 53/168; 53/498; 53/504; 221/2; 364/479
[58] Field of Search ............... 53/55, 54, 53, 53/52, 498, 494, 495, 504, 500, 168, 131.2, 131.4; 364/479, 478; 221/155, 87, 88, 9, 2, 123

[56] References Cited

U.S. PATENT DOCUMENTS

| | | | |
|---|---|---|---|
| 3,599,152 | 8/1971 | Williams | 340/147 |
| 3,606,959 | 9/1971 | Stonor | 221/2 |
| 3,618,819 | 11/1971 | Blackburn et al. | 221/2 |
| 3,780,907 | 12/1973 | Colburn et al. | 221/2 |
| 3,823,844 | 7/1974 | Linkemer et al. | 221/13 |
| 3,871,156 | 3/1975 | Koenig et al. | 53/168 X |
| 3,917,045 | 11/1975 | Williams et al. | 194/4 |
| 3,998,356 | 12/1976 | Christensen | 221/2 |
| 4,293,845 | 10/1981 | Villa-Real | 340/309 |
| 4,473,884 | 9/1984 | Behl | 364/479 |
| 4,573,606 | 3/1986 | Lewis et al. | 221/2 |
| 4,655,026 | 4/1987 | Wigoda | 53/55 |
| 4,695,954 | 9/1987 | Rose et al. | 364/413 |
| 4,717,042 | 1/1988 | McLaughlin | 221/3 |
| 4,725,997 | 2/1988 | Urquhart et al. | 368/10 |
| 4,733,362 | 3/1988 | Haraguchi | 364/479 |
| 4,785,969 | 11/1988 | McLaughlin | 221/2 |
| 4,847,764 | 7/1989 | Halvorson | 364/413.02 |
| 4,870,799 | 10/1989 | Bergerioux et al. | 53/168 X |
| 5,014,875 | 5/1991 | McLaughlin et al. | 221/2 |
| 5,097,652 | 3/1992 | Inamura et al. | 53/168 X |
| 5,105,600 | 4/1992 | DePoint, Jr. et al. | 53/168 X |
| 5,230,206 | 7/1993 | Christ | 53/168 X |

FOREIGN PATENT DOCUMENTS

| | | |
|---|---|---|
| 0342859 | 11/1989 | European Pat. Off. . |
| 0423893 | 4/1991 | European Pat. Off. . |
| 0439355 | 7/1991 | European Pat. Off. . |
| 0471150 | 2/1992 | European Pat. Off. . |
| 1584555 | 2/1981 | United Kingdom . |
| 2093249 | 8/1982 | United Kingdom . |
| 8700659 | 1/1987 | WIPO . |

*Primary Examiner*—James F. Coan
*Attorney, Agent, or Firm*—Vinson & Elkins

[57] ABSTRACT

A medication dispenser for use in a hospital or other medical setting comprises a plurality of containers for holding medication units, packaging apparatus for containing one or more medication units in a package and robotics for manipulating a selected container to transfer one or more medication units from the container directly to said package. Since medication is directly transferred from the container to the package, no cross-contamination occurs.

26 Claims, 14 Drawing Sheets

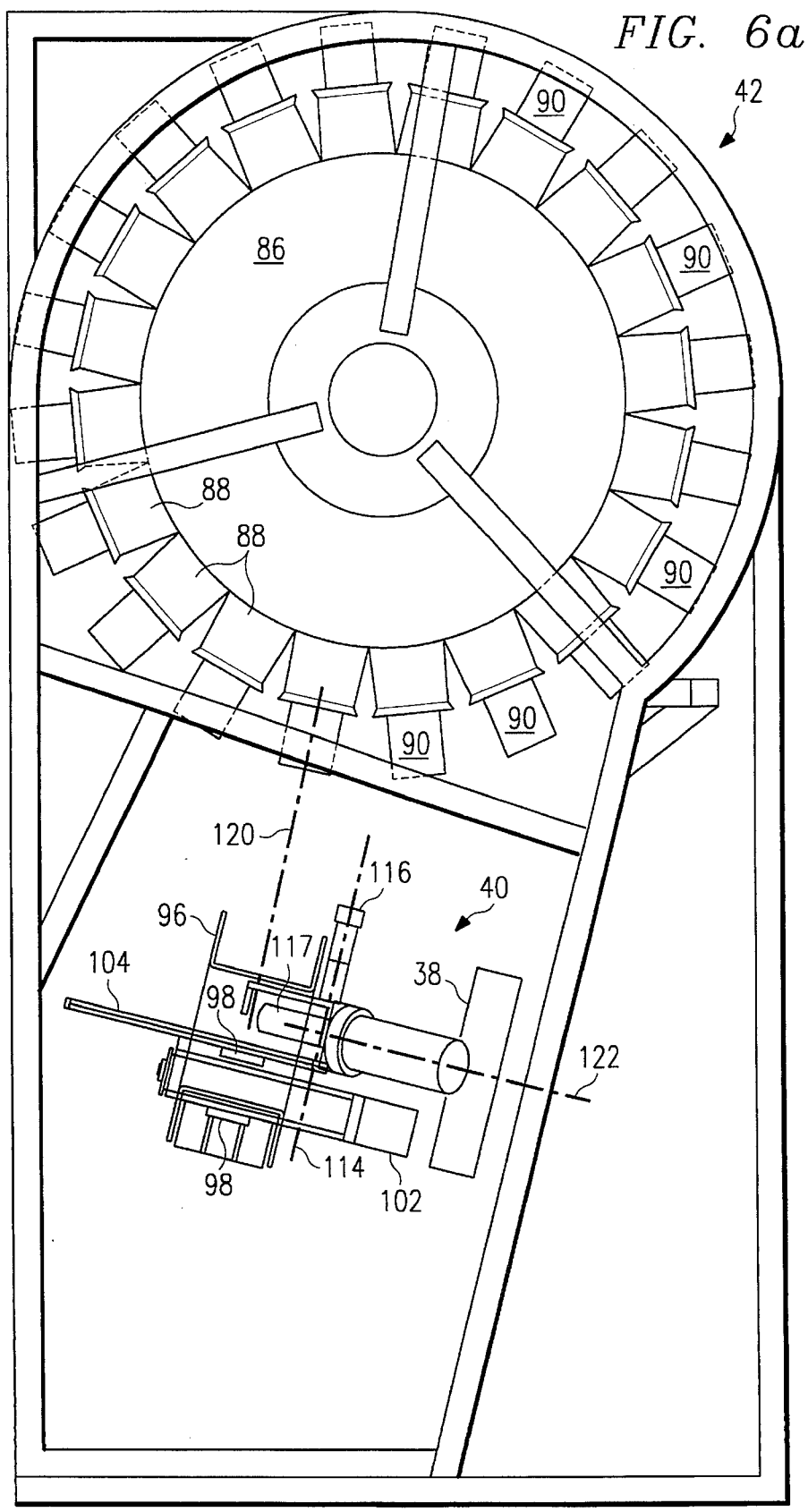

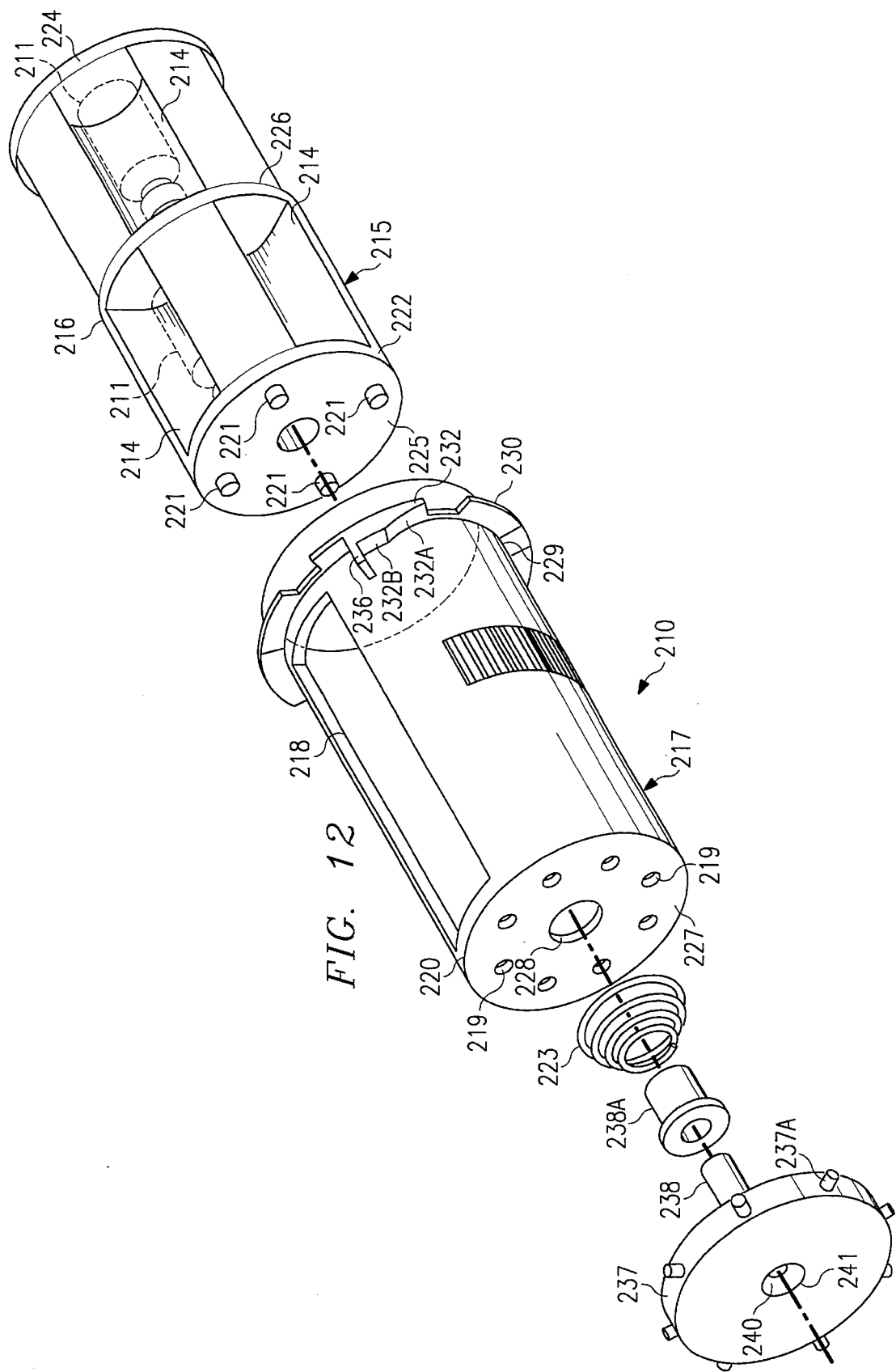

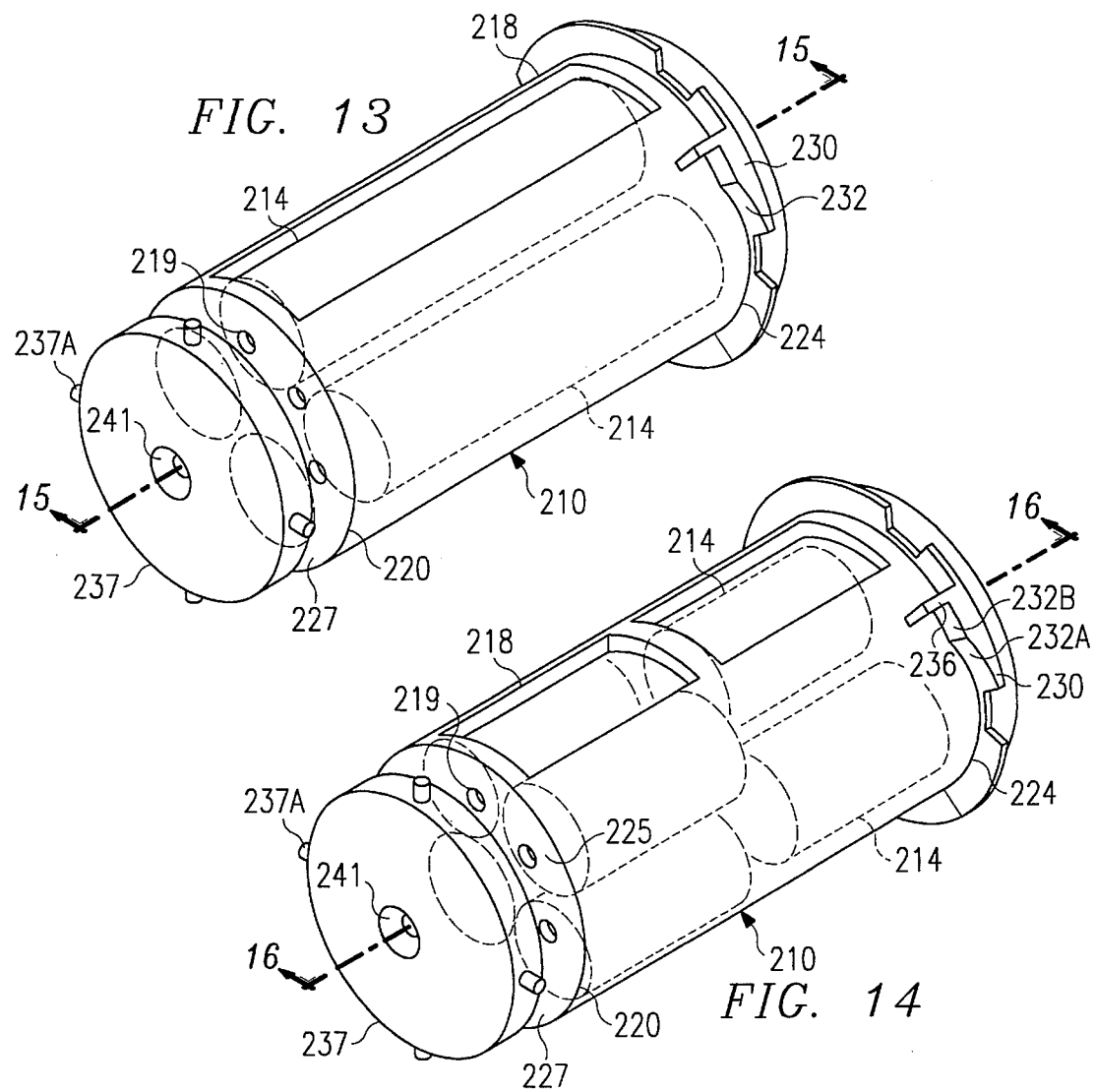
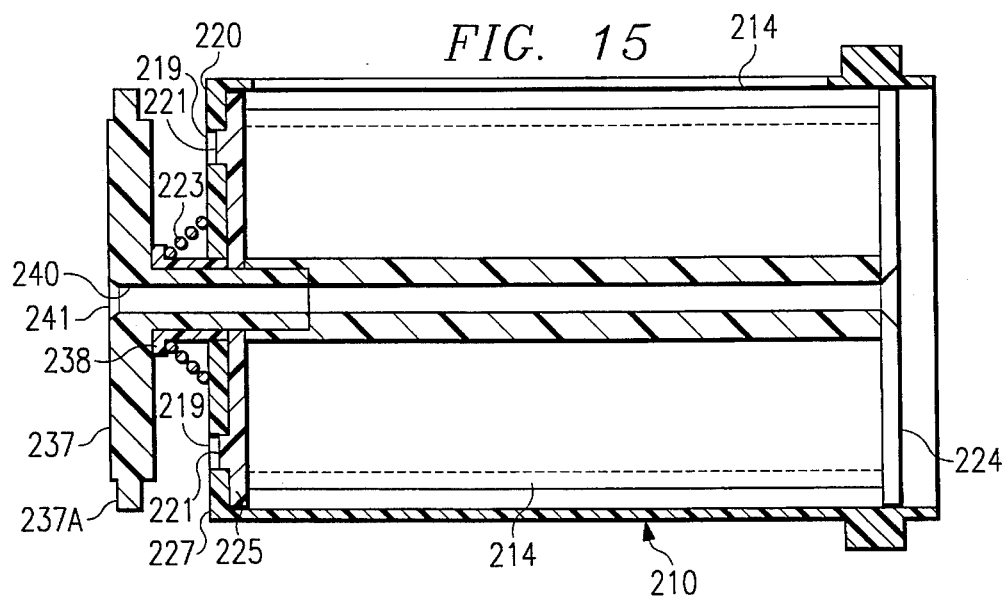

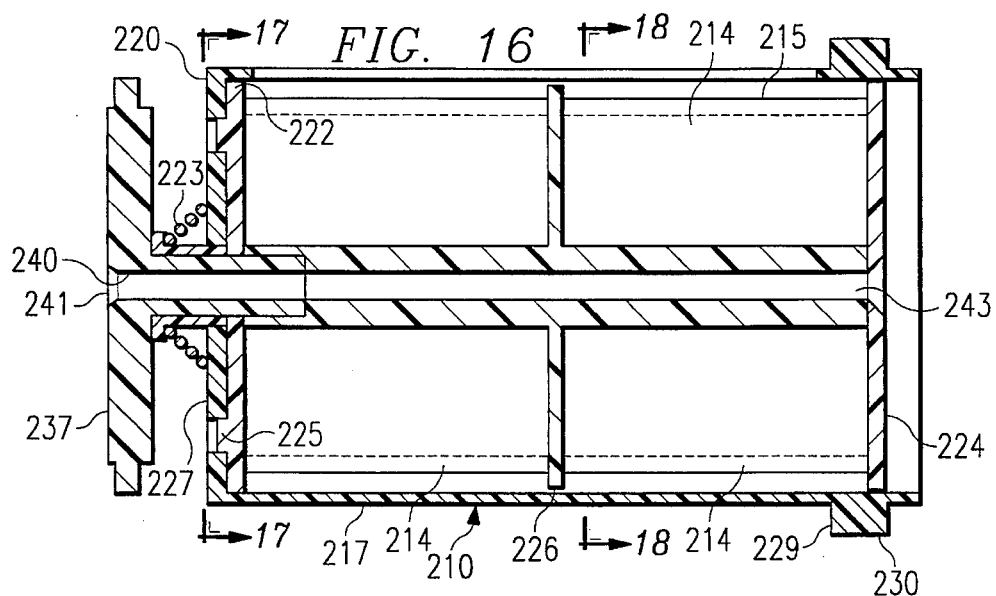
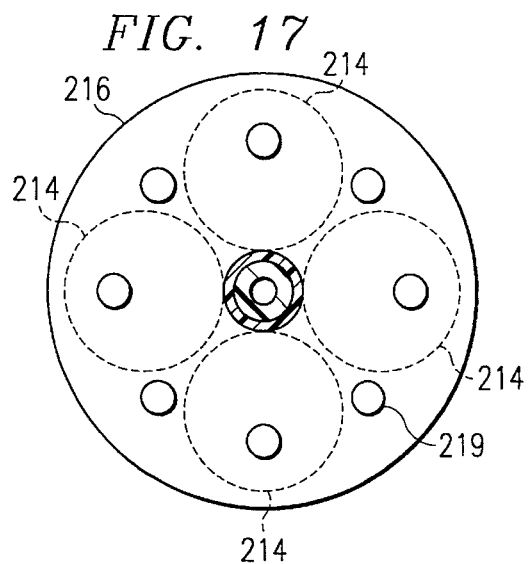
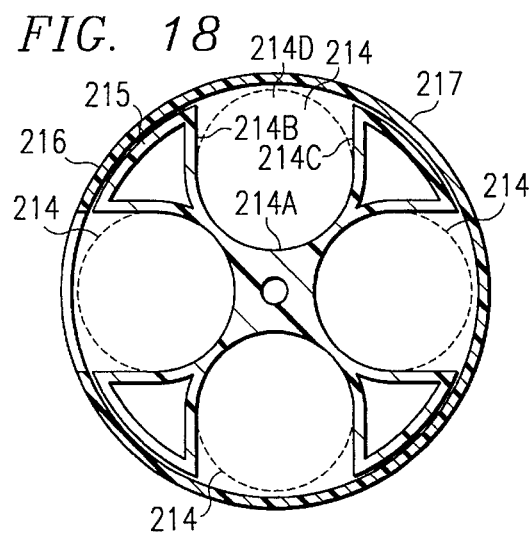
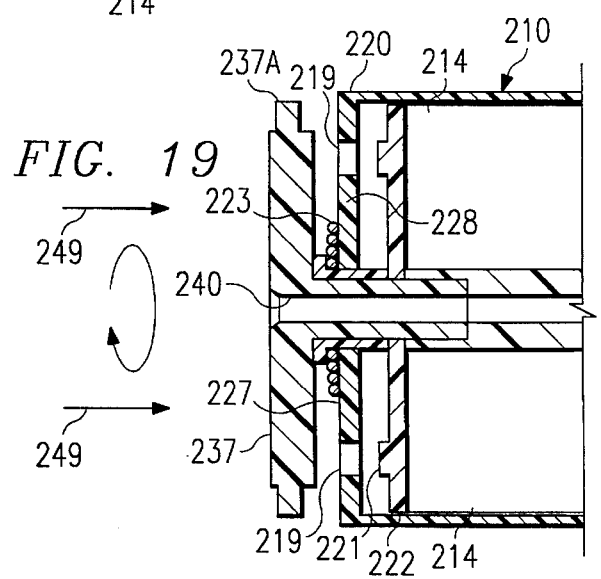

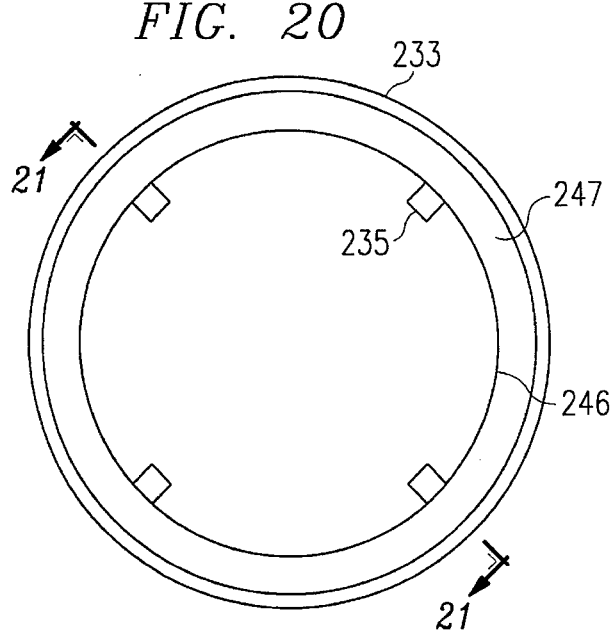
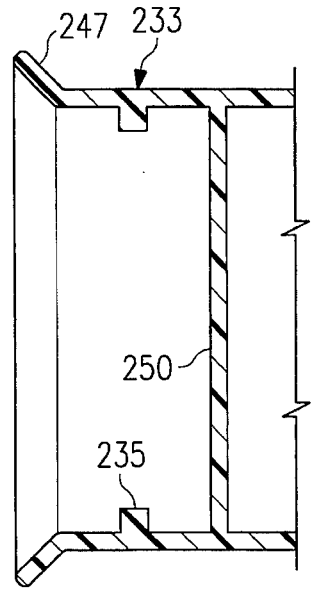
FIG. 20
FIG. 21
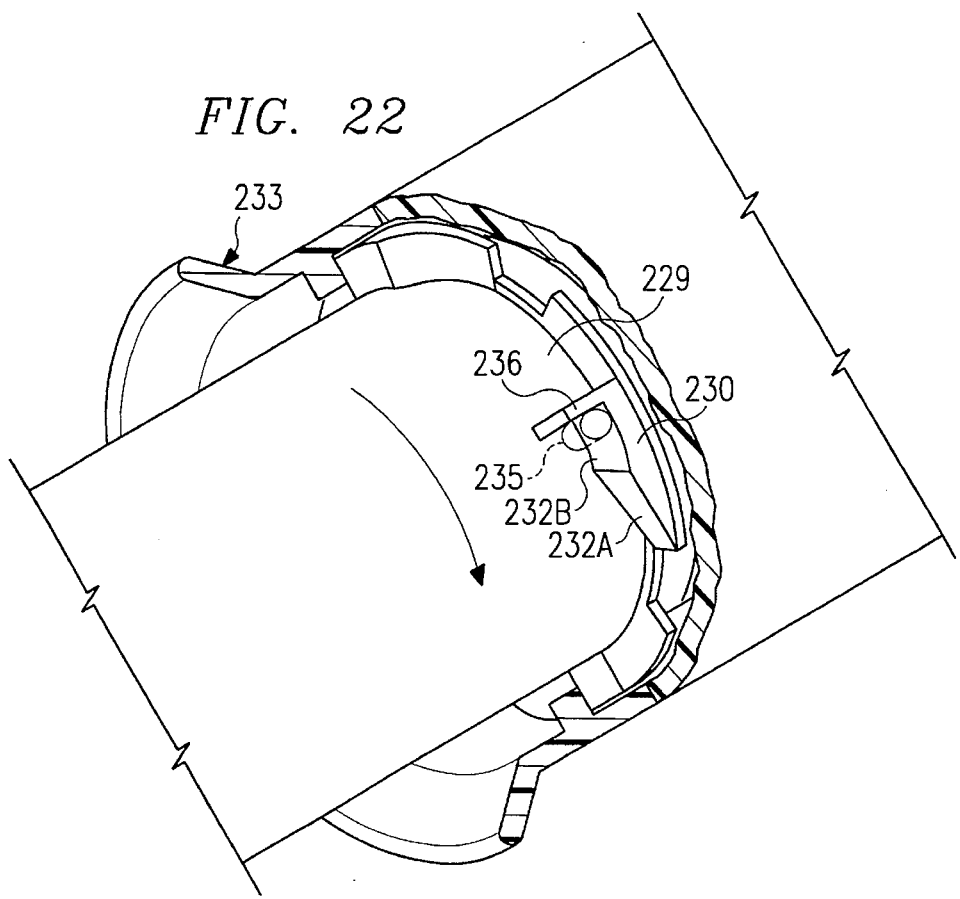
FIG. 22

MEDICATION DISPENSER SYSTEM

TECHNICAL FIELD OF THE INVENTION

This invention relates in general to medical dispensing machines, and more particularly to a medical dispenser system to provide medications to nurses in a hospital setting.

BACKGROUND OF THE INVENTION

The efficient and accurate distribution of medication in a hospital is an extremely important facet of patient care. In a typical hospital setting, medication orders are initiated by a physician, who contacts a pharmacist in the hospital's pharmacy. In response to the physician's request, the pharmacist enters information into the hospital's pharmacy computer system, which is typically implemented on a mainframe computer. The pharmacy computer system maintains a database of information concerning each patient in the hospital and performs a number of functions necessary to enable the pharmacy to efficiently distribute medications. For example, the pharmacy computer system maintains information on each patient, such as the patient's location in the hospital, whether the patient has any allergies to medication, the diagnosis, if any, for the patient, the patient's primary physician, the patient's personal data (height, weight, age, blood type), the date of admission, and so on. Further, the pharmacy computer system maintains a database of medications which may be ordered by the physicians. This database may include, for example, the NDC code for the medication, the manufacturer, the brand name, the generic name, the dosage form, the location of the drug in the pharmacy, and pricing information. For each medication ordered for a patient, the pharmacy system maintains a database of the medication ordered, the frequency of administration, start and stop dates (and times) for administration, and the nursing station to which the medication should be delivered. Pharmacy computer systems have been widely available since at least 1985. Their availability has greatly increased the accuracy and efficiency of the hospital pharmacy.

Based on the information in the pharmacy computer system, the pharmacy prepares the medications for each patient. Carts containing the medications are brought to the nursing stations, where the nurse retrieves the medication for his or her patients and then administers the medication. Typically, a separate container holding the medications for each patient are provided on the cart. To aid the nurses, a medication administration report (MAR) is provided from the pharmacy computer system, so that the nurse can verify that each patient has received all scheduled medication. Some common medications, such as pain relievers, are kept at the nursing stations for retrieval by the nurses.

This approach has significant problems. First, it is very time consuming and subject to human error. Second, it offers a very low level of security. Third, it has no means of accurately accounting for medication taken by the nurses, or other medical staff, from the nursing stations.

Some systems have been designed to increase security somewhat by providing a number of drawers, each containing several medications, which may only be opened after an authorization process. However, these systems can hold relatively few medications and cannot provide accurate accounting of the number of medications withdrawn from a drawer. Therefore, they provide little additional benefit.

Therefore, a need has arisen in the industry for a medication distribution system which reduces the time spent by pharmacy personnel and nursing staffs, with increased accuracy and accountability.

SUMMARY OF THE INVENTION

The medication dispenser of the present invention comprises a plurality of containers for holding medication units, packaging apparatus for containing one or more medication units in a package and robotics for manipulating a selected container to transfer one or more medication units from the container directly to said package.

This aspect of the present invention provides significant advantages over the prior art. Since medication is directly transferred from the container to the package, no cross-contamination occurs as part of the dispensing process. By placing dispensers around the hospital, the labor involved in providing medication to nurses is greatly reduced, and the accuracy in billing patients and maintaining the inventory of medications is greatly increased.

In one aspect of the present invention, a plurality of such dispensers are networked together and connected to a common database of patient information, typically a pharmacy software system. Medications are automatically dispensed responsive to a user request in accordance with the information in the database. The dispensers can communicate data for accounting and billing purposes, to the pharmacy system or to another system.

This aspect of the invention allows interfacing the dispensers with a pre-existing pharmacy system, which reduces costs for the hospital in equipment and training.

In another aspect of the present invention, one or more of the containers in the dispenser are operable to preload a predetermined number of medication units, typically a single medication unit, in a holding area until the medication units are requested. After the medication units are transferred to the packaging system responsive to a user request, new medication units are preloaded to the holding area in anticipation for the next request.

This aspect of the invention increases the speed with which medication units may be dispensed from the dispenser.

In another aspect of the present invention, various containers for storing bulk medication, such as pills, and for storing irregular shaped medications, such as syringes, ampules and vials, are provided.

This aspect of the invention increases the number of medications which can be automatically dispensed.

BRIEF DESCRIPTION OF THE DRAWINGS

For a more complete understanding of the present invention, and the advantages thereof, reference is now made to the following descriptions taken in conjunction with the accompanying drawings, in which:

FIGS. 6a–b illustrate top and front views, respectively, of the carousel and robotics subsystems;

FIG. 12 illustrates an exploded view of a module container used in the medication dispenser;

FIGS. 13 and 14 illustrate perspective views of different embodiments of the module container;

FIGS. 15 and 16 illustrate cross-sectional side views of different embodiments of the module container;

FIGS. 17 and 18 illustrate cross-sectional back views of the module container;

FIG. 19 illustrates a detailed cross-sectional side view of the module container in a state for independent rotation of the cylinder and dispensing container portions;

FIGS. 20 and 21 illustrate front and cross-sectional side views of the carousel receptacle;

FIGS. 22 and 23 illustrate a preferred embodiment for mounting a container to the receptacle;

DETAILED DESCRIPTION OF THE INVENTION

The preferred embodiment of the present invention and its advantages are best understood by referring to FIGS. 1–27 of the drawings, like numerals being used for like and corresponding parts of the various drawings.

Figure 1:
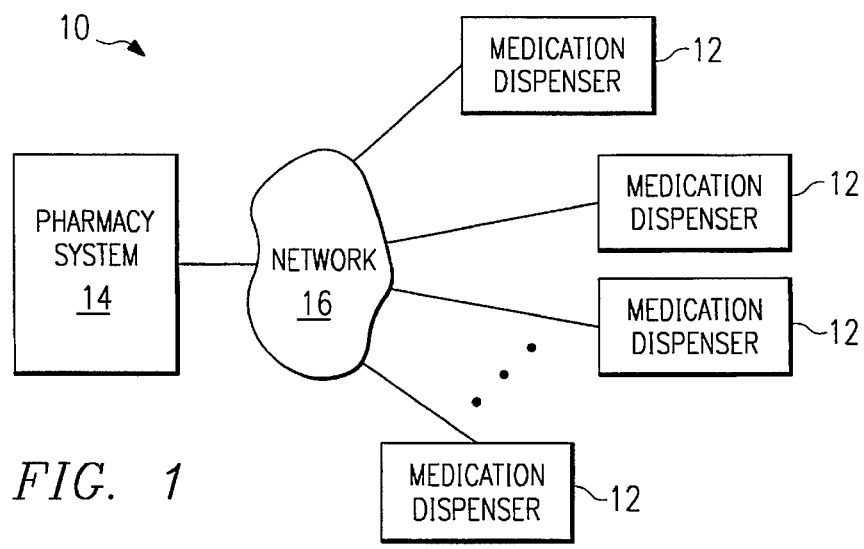
FIG. 1 illustrates a block diagram of a medication dispensing system.

FIG. 1 illustrates a block diagram of the overall medication dispensing system 10. The system 10 comprises a plurality of medication dispensers 12 coupled to a pharmacy computer system 14 and to each other through a network 16. In the preferred embodiment, the pharmacy computer system 14 can be a preexisting pharmacy system in order to reduce costs to the hospital and to facilitate the transition to the new method of distributing medication. Hence, pharmacy personnel can enter information into the pharmacy computer system 14 without change to their prior procedure. Alternatively, a pharmacy system designed specifically to operate in conjunction with the medication dispensers 12 may be provided. The medication dispensers 12, typically located at each nursing station, can retrieve information from the pharmacy computer system 14 through the network 16. In order to retrieve information from different pharmacy computer systems 14, an interface to the specific pharmacy system is provided.

Figure 2:
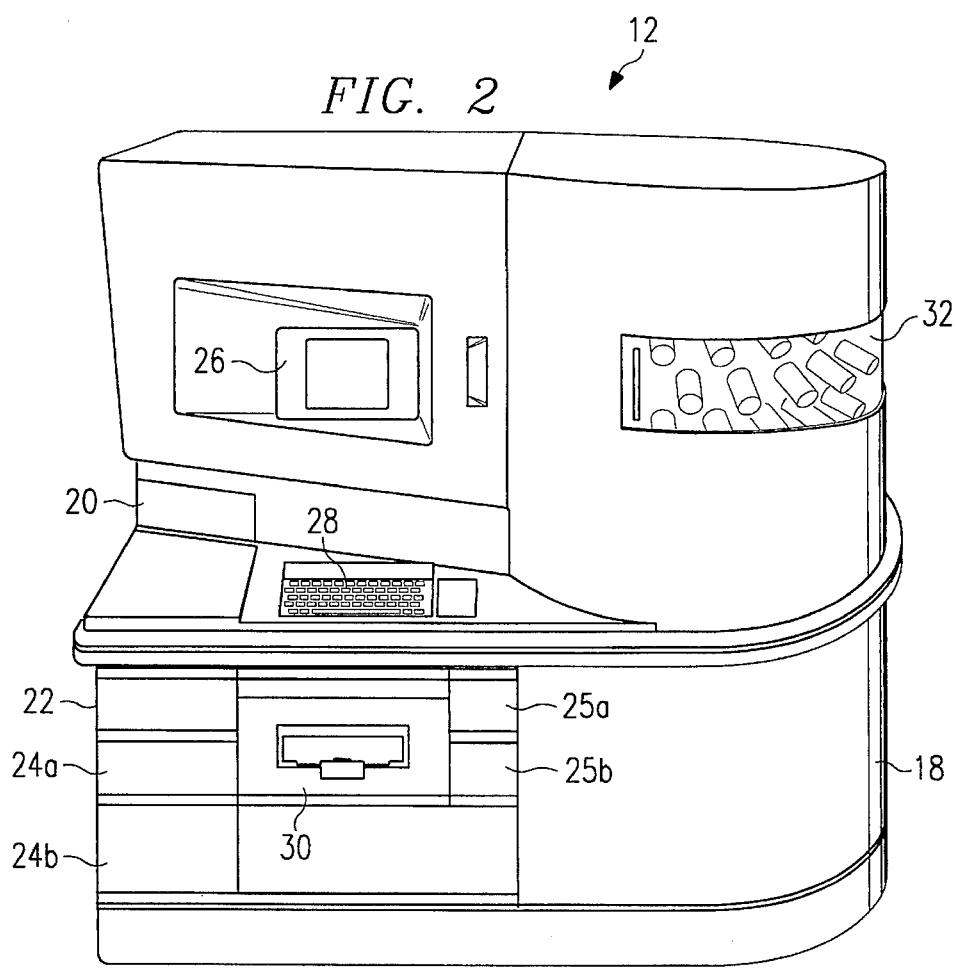
FIG. 2 illustrates a perspective view of a medication dispenser used in the medication dispensing system of FIG. 1.

A perspective view of a medication dispenser 12 is shown in FIG. 2. The outer housing 18 of the medication dispenser 12 includes two openings, stat opening 20 and a scheduled medication opening 22. Miscellaneous medication drawers 24a–b are also disposed within the housing 12. Return drawer 25a is provided for return of unused medications. Return removal drawer 25b allows the pharmacist to remove the unused medications. A video display 26, keyboard 28 and printer 30 are available at the front of the housing 18 for access by nursing and pharmacy personnel. Access to the carousel (described hereinbelow) of the medication dispenser 12 is provided through access door 32.

Figure 3:
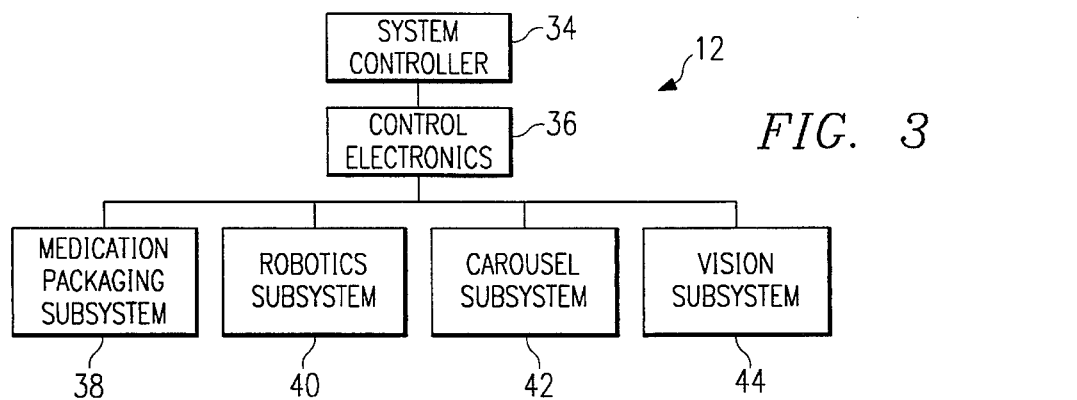
FIG. 3 illustrates a block diagram of the medication dispenser.

A block diagram of one of the medication dispensers 12 is shown in FIG. 3. The medication dispenser 12 comprises a system controller 34 coupled to control electronics 36. Control electronics 36 are coupled to a medication packaging subsystem 38, a robotics subsystem 40, a carousel subsystem 42 and a vision subsystem 44.

In operation, each medication dispenser 12 stores a plurality of medications in specialized containers, described in greater detail hereinbelow. Each container is operable to hold a plurality of medication units. In the preferred embodiment, typically 200 containers are available in each medication dispenser 12. The containers are prepared by the hospital pharmacy or by the pharmaceutical supplier and are labelled with a standard (human-readable) label and a machine-readable label containing all information required to meet industry requirements and for operation of the medication dispenser 12. The containers are loaded into the medication dispenser 12 by the pharmacist or other pharmacy personnel through the access door 32. The access door 32 is normally locked and can only be opened by designated personnel.

The access door 32 provides the pharmacy personnel with access to a small portion of the locations in the carousel subsystem 42 which hold the containers. After the pharmacy personnel load the medication modules through the access door 32 into the available positions in the carousel subsystem 42, the robotics subsystem 40 and carousel subsystem 42 reposition the containers to different locations on the carousel subsystem 42 so that the input locations available through the access door 32 will be available to receive additional medication containers. When a container has dispensed all of its medication units, the robotics subsystem 40 moves the empty container to a location accessible through the access window 32, so that the container can be removed and refilled.

As described in greater detail below, each container, in conjunction with the robotics subsystem 40, is operable to dispense a single medication unit. The dispensing process is initiated by a nurse who enters commands through the system controller 34 to retrieve medication for one or more patients. The information concerning the patients' medication requirements is stored on the pharmacy system 14 which is accessible to the medication dispenser 12 through the network 16. The system controller 34 performs the network functions for the medication dispenser 12. Once the nurse orders all or part of the authorized medication for each of the nurse's patients for a given medication round, the medication dispenser 12 retrieves each medication from its respective container and dispenses the medication to the medication packaging subsystem 38 where each individual medication unit is individually packaged. The medication packages for a given patient are labelled with information including the patient's name, room number, doctor's name and other data as required. In the preferred embodiment, the packages for each patient are connected as a strip, although they could be packaged as a set of separate packages. Each individual package is labelled with the medication and dose size. As individual medication is dispensed, the system controller 34 records the information.

In order to access the dispenser 12, the nurse must enter identification, such as an employee number and a secret password. The computer then allows the nurse to access information or order medication. The nurse will normally order medication for a complete round; however, in some cases, the nurse may order medication for less than all of the patients, and also may order less than an entire set of medication.

Medication which is not easily dispensed through the medication dispenser may be contained in the miscellaneous drawer 24. If such a medication is ordered, the drawer, which is normally locked, is released by the dispenser 12 to allow the nurse to access the medication.

Figure 4:
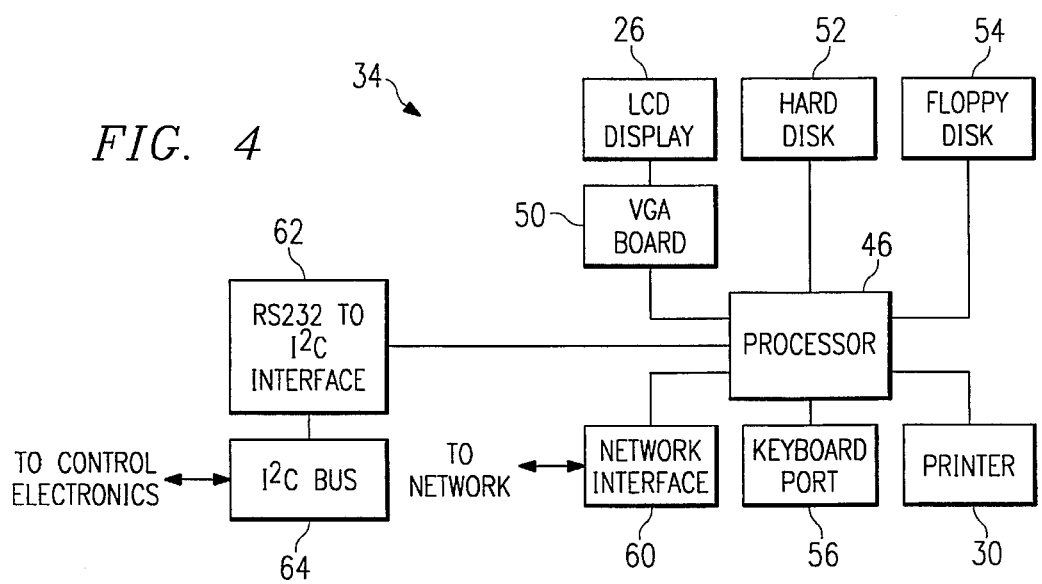
FIG. 4 illustrates a block diagram of a system controller used in the medication dispenser.

A preferred embodiment of the system controller is shown in FIG. 4. The system controller contains processing circuitry 46, such as an IBM-compatible computer motherboard, coupled to the display 26, such as a LCD display, via a graphics board 50, such as a VGA board. For mass storage, the system controller 34 is coupled to a hard disk 52 and a floppy disk 54. The nurse and pharmacy personnel enter data to the processor 46 through keyboard 28, which is connected to keyboard port 56. The processor 46 outputs information, such as medication administration reports, through a printer 30. Communication between the processor 46 and the network 16 is performed through network interface 60. The system controller 46 couples to control electronics 36 through a control electronics bus. In the illustrated embodiment, the control electronics bus is shown as an I$^2$C bus 64 coupled to the control electronics 36 via RS232-to-I$^2$C interface 62. Other bus types could also be used.

In operation, the system controller 34 acts as the interface between the medication dispenser 12 and the operators, such as nurses and pharmacy personnel. Responsive to an operator input, the system controller retrieves information through the network 16 regarding patient medication records and sends information to the control electronics 36. Responsive to the information from the system controller 34, the control electronics interfaces with the various subsystems 38–44 to dispense the requested medications.

The system controller 34 also communicates accounting information so that the patients are accurately billed. As medications are dispensed, the information on the quantity and type of medication dispensed for each patient is communicated to the pharmacy system (or other accounting system). Also, the information regarding the time of dispensing and the type and quantity of medication dispensed can be used to ensure that the medication was properly administered.

In the preferred embodiment, the system controller 34 also acts as a terminal to the pharmacy system. Hence, each dispenser 12 can be used to output various reports, such as MARs, from information stored in the pharmacy system. Consequently, additional terminals connected to the pharmacy system at the nursing stations are unnecessary.

The system controller 34 can also be used to output reports specific to the dispenser 12, such as a list of the inventory in the dispenser.

Figure 5:
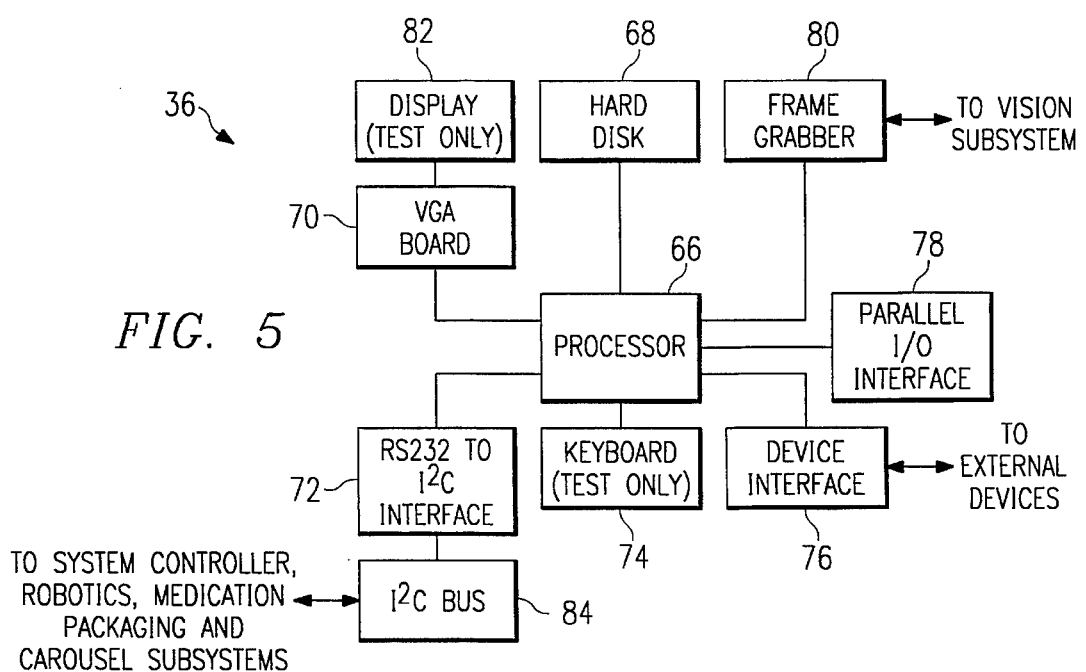
FIG. 5 illustrates a block diagram of the control electronics used in the medication dispenser.

FIG. 5 illustrates a block diagram of the control electronics 36. The control electronics comprises a processor board 66 coupled to a hard disk 68, a VGA board 70, an RS232-to-I$^2$C interface 72, keyboard 74, device interface 76, parallel interface 78, and frame grabber 80. The graphics interface 70 may be coupled to a display 82 and keyboard for test purposes. The RS232/I$^2$C interface 72 is coupled to an I$^2$C bus 84 which connects the control electronics 36 to the system controller 34 and to the robotics, medication packaging, and carousel subsystems 38–42. The device interface 76 couples the processor board 66 to external devices, such as additional cabinets. The frame grabber 80 receives image data from the vision subsystem 44.

In operation, the control electronics provides robotics control calculations and movement scheduling for the packaging subsystem 38, the robotics subsystem 40 and the carousel subsystem 42. The processor 66, in conjunction with the frame grabber 80, reads labels from the containers and performs medication singulation (described in greater detail in connection with FIGS. 11a–f below).

The control electronics 36 maintains a database of information concerning the contents of the dispenser. In response to a request, the control electronics 36 determines whether all requested medications are available. If not, the requesting person is notified. In the preferred embodiment, the pharmacy personnel, upon entering medication order data into the pharmacy system, will be notified if a medication is not present in the dispenser associated with the patient's location in the hospital, so that the medication can be taken to that location.

The database maintained in the control electronics 36 also tracks the location of each medication in the carousel subsystem 42 for retrieval by the robotics subsystem 40. As medication is dispensed, the database is updated to reflect the remaining number of the medication units in the container.

Figure 6B:
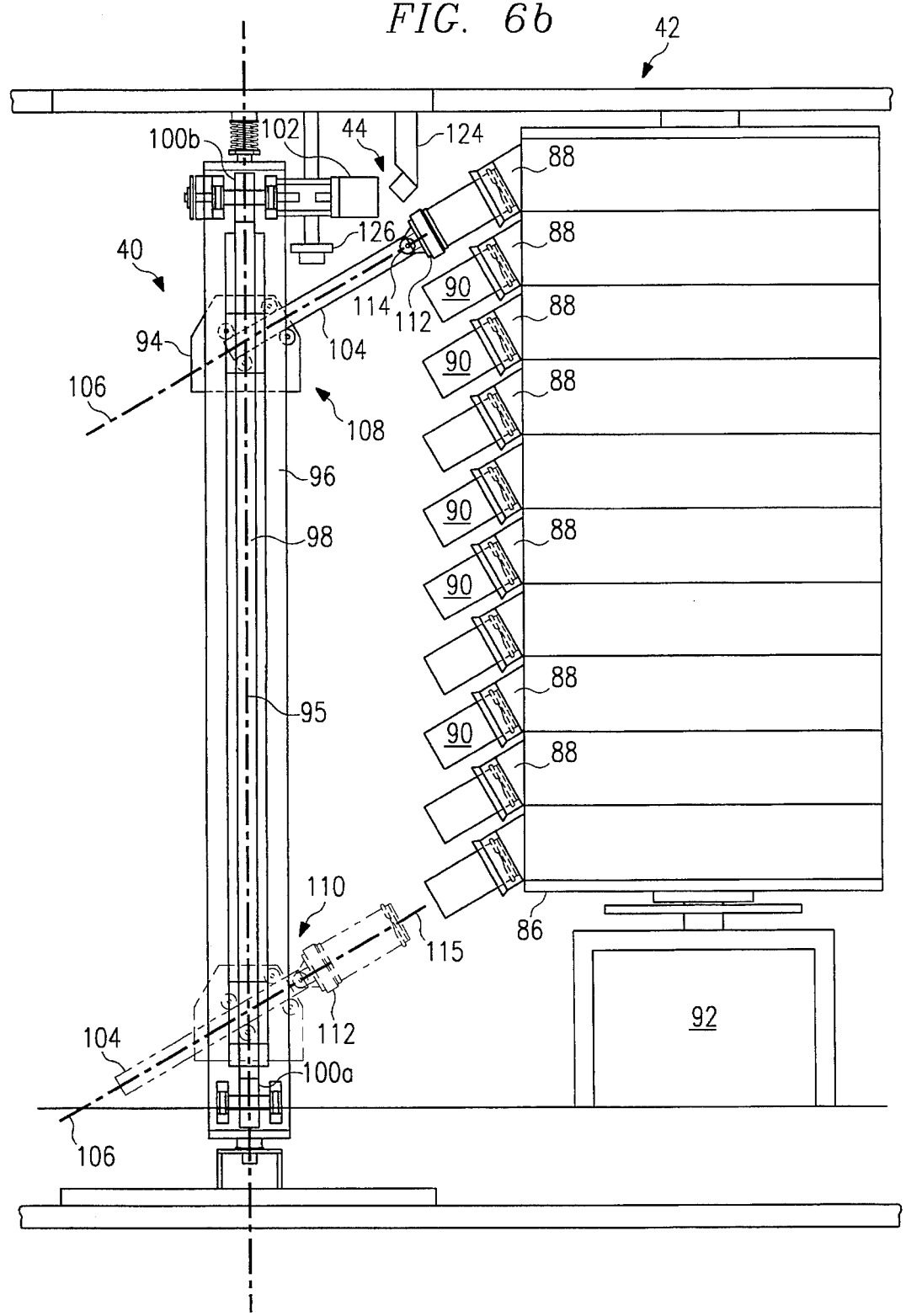
Figure 7A:
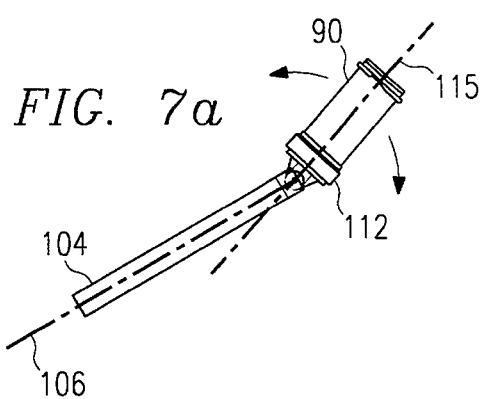
FIGS. 7a–b illustrate side and front views of the extend arm and end effector in use with a medication container.
Figure 7B:
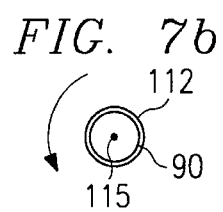

FIGS. 6a–b illustrate top and front views of the robotics subsystem 40, carousel subsystem 42 and vision subsystem 44. The robotics subsystem 40, carousel subsystem 42 and vision subsystem 44 interact to dispense a single medication unit from a selected container to the medication package subsystem 38. The carousel subsystem 42 comprises a rotating column 86 onto which a plurality of receptacles 88 are disposed. Each receptacle is operable to hold a container 90. Different types of containers for holding various medication units are described in greater detail in connection with FIGS. 8–9 and 12–23.

The column 86 is rotated by a motor 92 which is controlled by the control electronics 36. The control electronics is operable to position the column 86 such that a row of containers 90 is accessible to the robotics subsystem 40. The control electronics 36 maintains a database of which medication is in each of the receptacles. Hence, for a given medication, the control electronics can control the motor 92 to rotate the column 86 to the proper position for retrieval of the desired medication by the robotics subsystem 40.

The robotics subsystem 40 provides for manipulation of the containers 90 to prepare a single medication unit for dispensing and for dispensing the medication unit to the packaging subsystem 38. A base plate 94 using radial bearings is slideably engaged within a vertical track 96. The base plate 94 is connected to belt 98 which is a continuous belt wrapped around bearings 100a–b. Bearing 100b is driven by motor 102 to rotate belt 98 and, hence, vertically position base plate 94 along a vertical axis 95. Motor 102 is controlled by the control electronics 36.

Base plate 94 is coupled to extend arm 104. Extend arm 104 extends and retracts along an extend axis 106 responsive to a pneumatic cylinder (not shown). Extend arm 104 is shown in an extended position at 108 and in a retracted position (in phantom) at 110. In the preferred embodiment, the pneumatic cylinder positions the extend arm 104 in either the extended or retracted position, but is not continuously variable in between. However, using electromechanical technology, an extend arm 104 could be provided to have variable positions along the extend axis 106.

The extend arm 104 is coupled to an end effector 112. The end effector 112 is operable to rotate about a pitch axis 114 and to rotate about a roll axis 115 (see FIGS. 7a–b). The pitch of the end effector 112 is controlled by pitch motor 116. Rotation of the end effector 112 is controlled by roll motor 117. The pitch motor 116 and roll motor 117 are controlled by the control electronics 36.

The vertical track 96 and all components attached thereto may be rotated about the vertical axis 95 by the control electronics 36. Rotation around the vertical axis is referred to as "yaw." In the preferred embodiment, control of the yaw is restricted to positioning the extend arm 104 between first yaw position shown at 120 and second yaw position shown at 122 (see FIG. 6a). At first yaw position 120, the robotics subsystem 40 is operable to remove and replace containers 90 in the carousel 86. At second yaw position 122, the robotics subsystem 40 is operable to dispense medication to the packaging subsystem 38.

The vision subsystem 44 comprises two optics systems, singulation optics 124 and a container identification optics 126. The container identification optics 126 may comprise, for example, a bar code or a block code scanner. The container identification optics 126 reads a label disposed on the outside of each container which identifies its contents. The contents (as defined by the label) of a chosen container is compared with the specified medication in order to verify that the correct medication is being dispensed. The container identification optics, in conjunction with the control electronics, also determines whether the medication in the module has reached its expiration date.

The singulation optics 124, in conjunction with the control electronics 36, ensures that a single oral medication is staged to be dispensed from the container. A more detailed description of the staging operation and the singulation optics 124 is described in connection with FIGS. 8–12.

Figure 8:
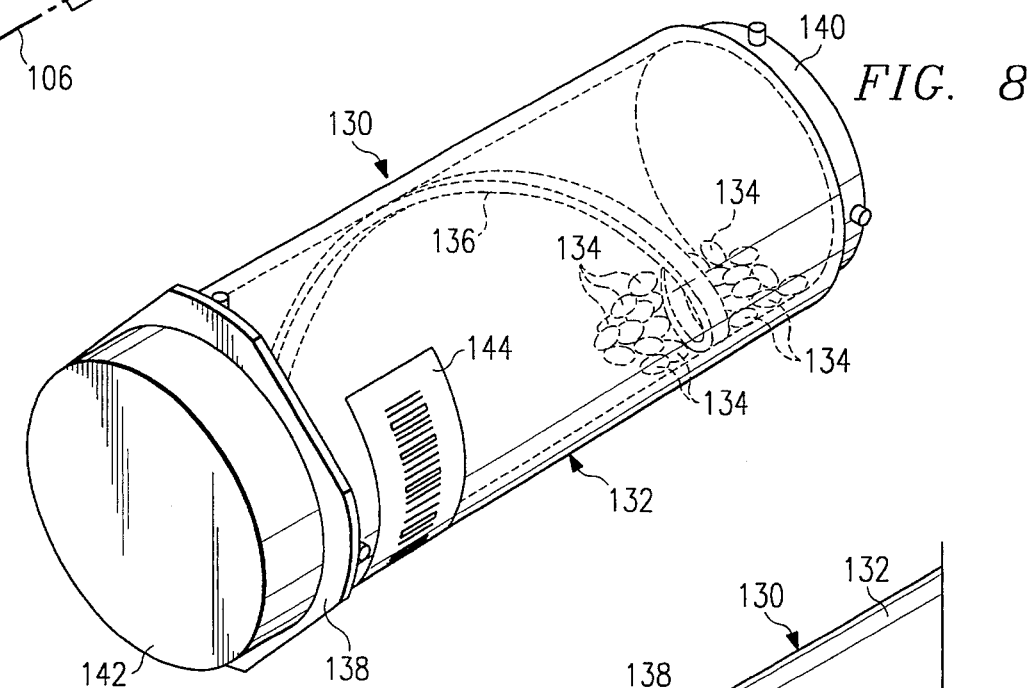
FIGS. 8–9 illustrate perspective and exploded views of a bulk medication container.
Figure 9:
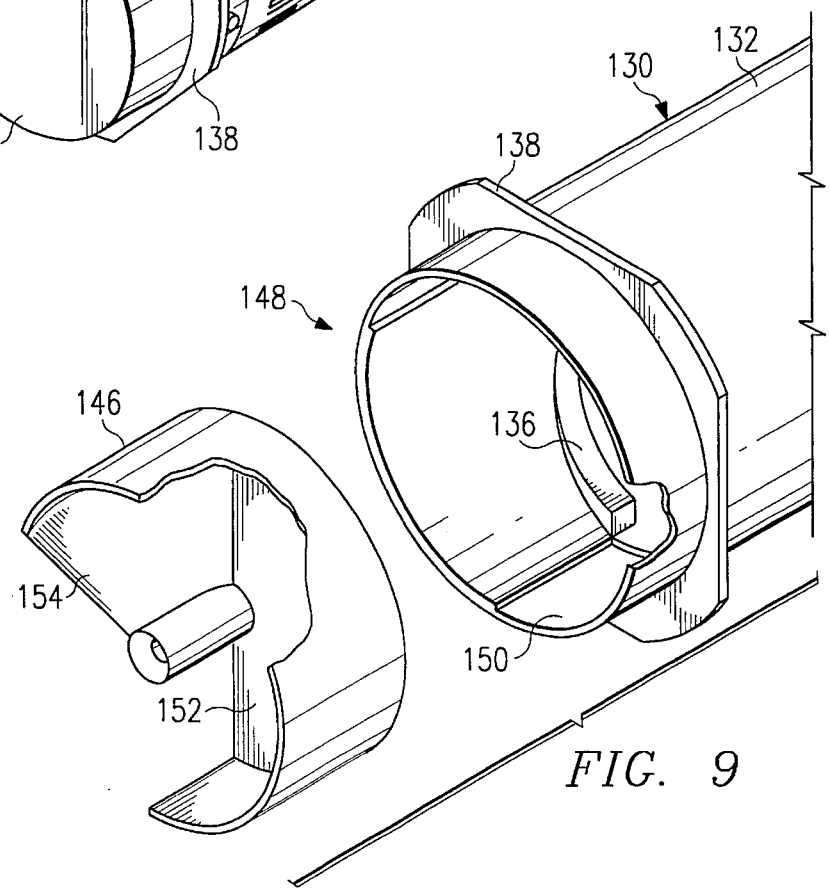

FIGS. 8–9 illustrate a container 130 used to dispense single units of bulk medication, such as pills, tablets and the like. This container is the subject matter of U.S. Pat. No. 5,213,232, to Kraft et al., issued May 25, 1993, and assigned to the assignee-of-interest, which is incorporated by reference herein. The bulk medication container 130 comprises a container portion 132 for containing a plurality of pills 134 in bulk form. Inside the container portion 132, there is a helical ridge 136 which acts as a ramp for the pills. Interface 138 couples the container to the receptacles 88 of the carousel subsystem 42. Interface 140 interfaces the container 130 with the robotics subsystem. A cap 142 is used to seal the container 130 while the pills 134 are stored outside the dispenser 12; to load the container 130 into the dispenser 12, the cap 142 is removed and the interface 138 is attached to a receptacle 88. A label 144 is adhered to the exterior of the container 130. The label 144 contains information on the medication stored within container 130. This information is used for the database internal to the dispenser 12 and for verification prior to dispensing medication. The label 144 can take a variety of formats, such as one of a number of bar codes or block codes.

FIG. 9 illustrates an exploded view of the bulk medication container 130. As can be seen, a discharging element 146 is disposed in the open end 148 of the bulk medication container 130. The discharging element 146 comprises a holding area 152 and a discharge ramp 154. In the preferred embodiment, the discharging element 146 is removably seated within the open end 148 as shown by grooved section 150. The grooved section 150 mates with the outer wall 151 of the discharge element 146.

In operation, the container 130 is manipulated by the robotics subsystem 40 to place (or "stage") a single medication unit in the holding area 152. While it may be possible to load a predetermined number of medication units in the holding area 152, staging a single medication unit is preferred because it allows the holding area 152 of each container to be preloaded (i.e., loaded prior to a request for the medication) with the most likely quantity to be requested. In the preferred embodiment, each container 130 in the carousel subsystem 42 is preloaded. The preloading occurs upon loading the container into the dispenser 12 through the access door 32 and after a medication unit is dispensed to the packaging subsystem 38. For efficient operation, the containers 130 can be preloaded while there is no dispensing activity ongoing. Hence, for a given request, at least one medication unit for each medication will be preloaded into the holding area 152 of the container 130 for fast transfer to the packaging subsystem 38.

To place a single medication unit in the holding area 152, the sequence shown in flow chart of FIG. 10 is implemented. In block 156, the container 130 is rotated at a predetermined pitch angle. In the illustrated embodiment, the pitch angle is initially set to a predetermined angle relative to the horizontal, and is adjusted during use. The initial angle is determined by a number of factors, including the type of medication and the fullness of the container as loaded. While many containers are initially full, some containers may have only the number of medication units for a specific patient. In the preferred embodiment, data on each type of medication is maintained in an internal database to provide the best estimate of an initial angle based on the quantity of units in the loaded container.

To load a pill (or other medication unit) into the holding area, the container 130 is rotated 270° (or another predetermined angle) about the roll axis 115 by the roll motor 117 then is rotated 270° in the opposite direction. When the end effector rotates about the roll axis 115, medication units travel up the helical ridge 136 in single file. The end effector 112 stops rotating when either three rotation cycles have been completed without detecting a pill in the holding area (decision block 158) or one or more pills are detected in the holding area (decision block 160). In the preferred embodiment, if three rotation cycles are completed without the detection of any pills in the holding area, the pitch angle is decreased by one degree and the rotation count is reset in 162. Thereafter, the sequence provided by block 156, 158 and 160 is repeated. When one or more pills are detected in the holding area (block 160), the rotation of the container 130 is stopped in block 164. If more than one pill is identified in the holding area 152 in block 166, the container is rotated one full rotation in the opposite direction to return all pills from the holding area 152 to the container (block 168). Also, the pitch angle is increased by one degree and the rotation count is reset. Thereafter, the robotics subsystem continues rotation of the container at block 156. If a single pill is identified in the holding area in block 166, the pitch angle of the container 130 is increased (block 170) in order to return any remaining pills on the helical ridge 136 to the bottom of the container, such that no pills will transfer from the helical ridge 136 to the holding area 152 during subsequent movement of the container 130.

Figure 10A:
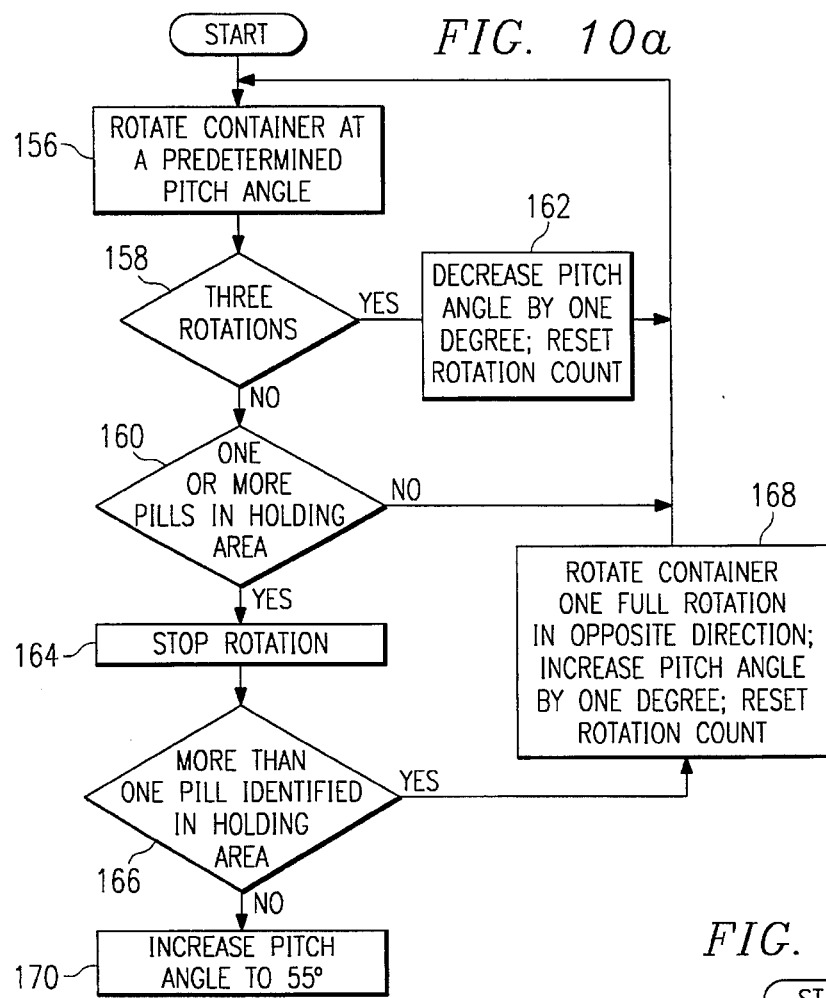
FIGS. 10a–c illustrate flow charts describing operation of the robotics and vision subsystems to dispense a single pill from the bulk medication dispenser of FIGS. 8 and 9.
Figure 10C:
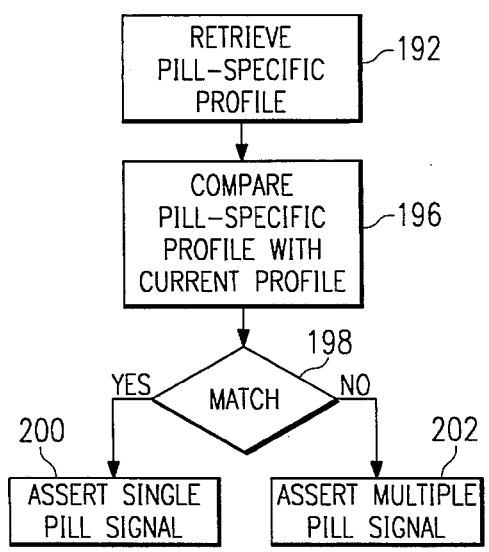
Figure 10B:
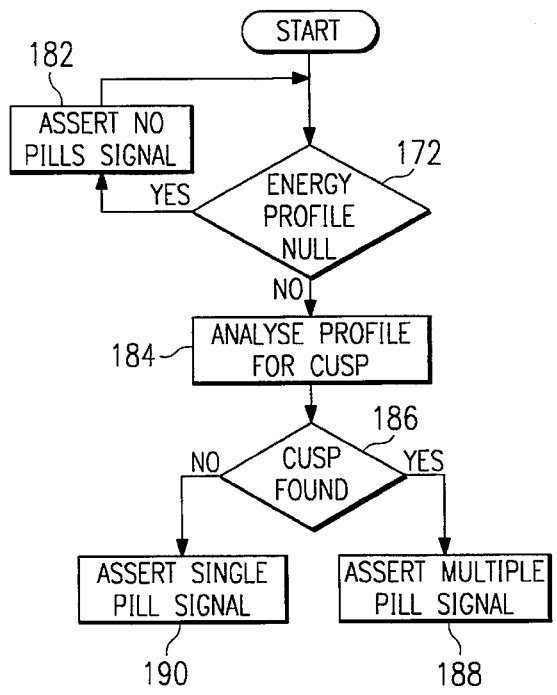

In FIG. 10b, the detection of medication units in the holding area 152 is described in greater detail. In decision block 172, an energy profile is monitored to determine whether one or more pills are in the holding area 152. The energy profile is generated from the light reflected off the pills in the holding area and received by the singulation optics 124. To enhance the energy profile, the optics may include LED's or another light emitting device to increase the amount of light. The image from the singulation optics 124 is transferred to the frame grabber 80.

Figure 11A:
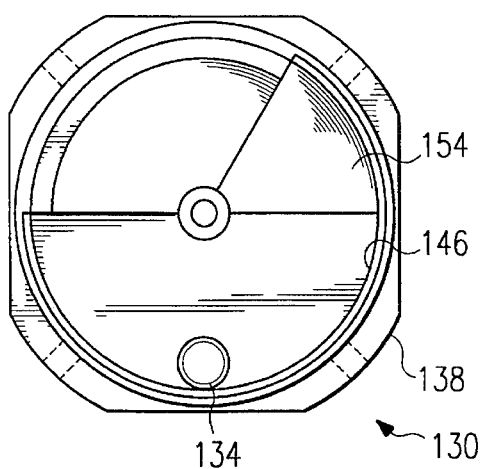
FIGS. 11a–f illustrate pill configurations and respective energy profiles used in the vision subsystem singulation process.
Figure 11B:
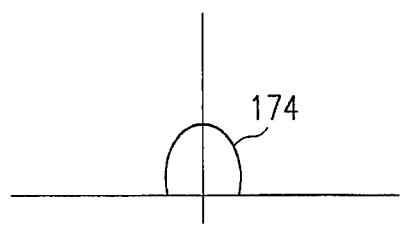

FIGS. 11a–e illustrate the profiles associated with various orientations of pills in the discharging element 146. In FIG. 11b, the energy profile for a single round tablet (see FIG. 11a) is shown. The energy profile is derived by the control electronics from the output of the singulation optics, which is captured by the frame grabber 80 as needed. The control electronics 36 performs image processing on the data contents of the frame grabber 80 to derive the energy profile corresponding to the pills disposed in the discharging element 146.

Figure 11C:
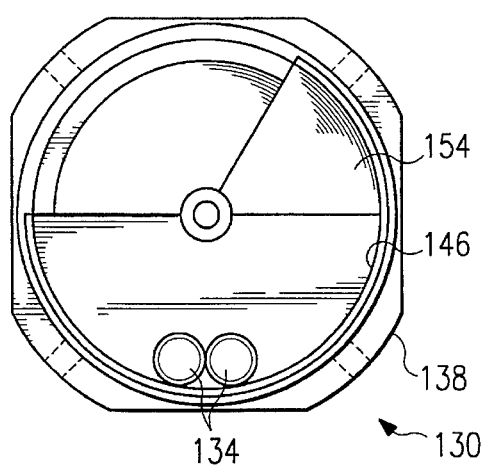
Figure 11D:
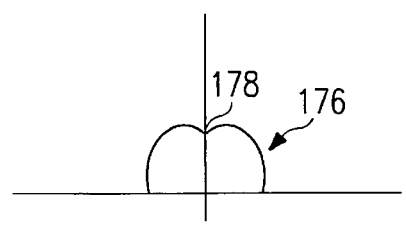

In FIGS. 11a–b, a single pill and its energy profile 174 are illustrated. As can be seen, the energy profile 174 is relatively smooth. In FIGS. 11c–d, an energy profile for pills which are side-by-side or partially overlapping is shown. Responsive to the outline of the pills in FIG. 11c, a corresponding energy profile 176 is generated. The energy profile 176 has a cusp 178 corresponding to the cusp 180 found between the two pills 134 in the discharging element 146.

Referring again to FIG. 10b, so long as the energy profile is null, a signal is asserted indicating that there are no pills in the discharging element 146. Assertion of this signal causes the robotics to rotate the container (until the three rotations are complete). Once one or more pills are disposed within the discharging element 146, the energy profile is no longer null in block 172 and thus, in block 184, the energy profile is analyzed to determine whether there are any cusps. If a cusp is found in decision block 186, a "multiple pill" signal is asserted by the control electronics 36. If no cusp is found, then the "single pill" signal is asserted by the control electronics 36. The "multiple pill" signal and "single pill" signal are used in decision block 166 of FIG. 10a.

Figure 11E:
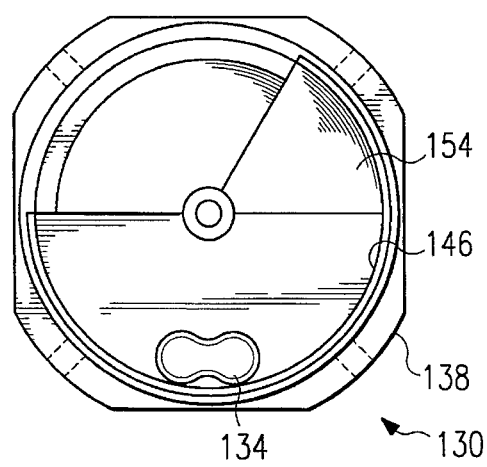
Figure 11F:
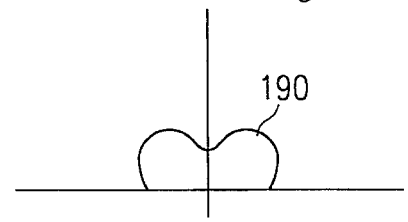

FIG. 10c and FIGS. 11e–f illustrate a second embodiment of the present invention wherein a pill-specific profile is compared with the profile generated by the singulation optics 124 and the control electronics 36 to determine whether more than one pill is loaded in the holding area 152.

Whereas the singulation method shown in FIG. 10b and FIGS. 11a–d is pill-independent, i.e., it can be used without any information regarding the type of pills being singulated, the method shown in FIGS. 10c and 11e–f use pill-specific information to improve the quality of the singulation process. This embodiment is useful for use with odd-shaped pills, such as the bow-tie shaped pill 134 shown in FIG. 11e, which would produce an energy profile 190 shown in FIG. 11f. Such a profile may be interpreted as having a cusp which would indicate multiple pills under the previously described embodiment, even though a single pill was in the discharging element 146.

In this embodiment, pill-specific information is retrieved in block 192 of FIG. 10c which corresponds to the profile which should be obtained if a single pill is in the discharging element 146. The pill-specific information may be stored in a database in the memory of the control electronics 36 or may be specified on the label 144. Information in the profile would include, for example, the height, depth, and width dimensions of the pill and shape type, such as round, capsule, oblong and bow-tie. The pill-specific information is used in a three dimensional comparision with the profile determined from the image provided by the singulation optics 124 in block 196. If the energy profile matches within a given threshold in decision block 198, the "single pill" signal is asserted in block 200. If there is not a match in block 198, the "multiple pill" signal is asserted in block 202.

The pill-specific approach is also useful for capsules, where two or more capsules may overlap in the holding area. Because of the shape of the capsules, a cusp may not be apparent from the energy profile. However, the width dimension would be in excess of the pill-specific dimension, and would therefore cause a multiple pill signal. Further, the pill-specific approach may be useful in an embodiment where a predetermined number of pills greater than one are being detected.

Even using pill-specific information, it is possible that singulation errors may occur, albeit rarely, if two pills are positioned such that one pill is directly in front of the other. This situation can be overcome by using two cameras to view the holding area 152 from different directions (or by adjusting the position of the holding area relative to the camera to provide two or more views) such that one pill cannot completely obscure the other.

Referring to FIG. 12 a container 210 for holding larger objects is shown in an exploded view. Container 210 is used for dispensing single regular or irregular shaped units upon rotation of the apparatus 210. In this particular embodiment, there is shown irregular shaped units 211 such as, for example, a syringe or ampules, located in compartments 214. These compartments 214 are located in a dispensing container 215 having generally concave walls 216. Compartments 214 are formed within the generally concave walls 216 having three sides 214A, 214B, 214C and one open side 214D. The irregular or regular units 211 can be discharged from the compartment 214 through the open side 214D of the compartment 214 to the outside upon rotation of the compartment 214 to a position that gravity would cause the irregular or regular units 211 to fall.

A cylinder 217 is provided which has at least one slot 218 therein for selectively providing an opening for selective dispensing of the irregular and regular units 211; the cylinder 217 is mounted exteriorly of the dispensing container 215.

The dispensing container 215 and the cylinder 217 are sized, as can be seen in FIG. 12, such that they can be mounted in a nesting relationship and for free rotation therebetween. It will be apparent that when slot 218 is rotated over a compartment 214 in the dispensing container 215, that compartment 214 will be open to discharge its units 211. The container 215 and cylinder 217 can be positioned such that gravity will cause the irregular or regular shaped units 211 to discharge from the compartment 214 accessed through slot 218.

In the embodiment shown in FIGS. 12, 13, and 15 (along with FIGS. 17 and 18), the dispensing container 215 is comprised of compartments 214 which are arranged in a circular fashion about the axis of dispensing container 215 which has concave walls 216. The top end 224 of the dispensing container 215 is closed and the bottom end 225 is also closed to provide a closure to the compartments 214 for the retention of the units 211 to be dispensed.

In the embodiment shown in FIGS. 14 and 16 (along with FIGS. 17 and 18), an additional septum 226 is provided mid-way along the dispensing container 215 to provide for an eight unit dispensing container 215 instead of a four unit dispensing container as shown in FIGS. 13 and 15. It would be understood by those skilled in the art, that the length of the container and the number of septums and the compartments created could be varied depending upon the size of the container and the size of the units 210 to be dispensed without departing from the scope and contents of this invention.

To selectively rotate the cylinder 217 and the dispensing container 215 either together as a unit or, alternatively, independently as separate pieces so that the slot 218 is brought into new positions for dispensing a unit 211 requires the selective engaging of the container 215 and cylinder 217. As shown in FIGS. 15, 16 and 19, female members 219 are located on the lower portion 220 of the cylinder 217 which are functionally related to male members 221 located on one end 222 of the dispensing container 215. A resilient member, spring 223, is provided for creating a force engaging or disengaging the male and female members 219 and 221. Thus, when resilient member 223 is expanded, the male and female members 221 and 219 are mated to provide engagement of the cylinder 217 and the dispensing container 215. When the resilient member is compressed, the cylinder 217 and dispensing container 215 may be rotated independent of each other.

Cylinder 217 has located on its other end 229 members 230 for allowing the engagement and holding of said cylinder 217 and dispensing container 215 in the receptacles 88. By holding the cylinder 217 in a fixed position (with the slot 218 upwards) in a receptacle 88, the robotics subsystem 40 rotates the dispensing container 215 inside said cylinder 217 for the alignment of slot 218 over a selected compartment 214.

Figure 23:
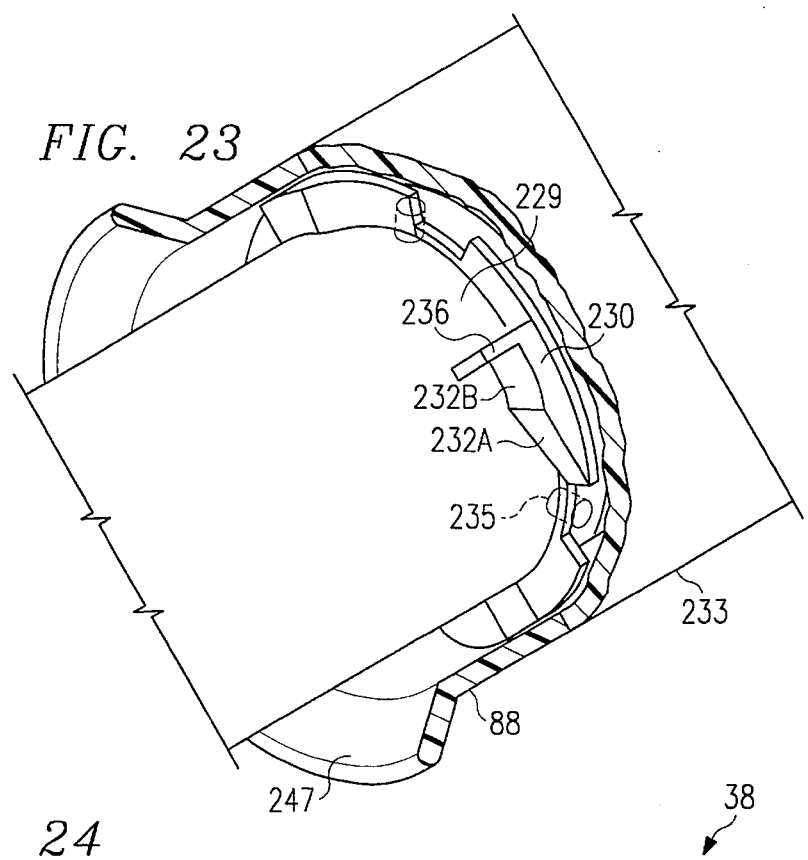

As shown in FIG. 23, the members 230 are composed of at least two pins projecting from cylinder 217 or at least two raised inclined surfaces 232 which project upward from the cylinder 217. These are designed to be engaged with the receptacle 88. In the embodiment shown in FIGS. 20, 21, and 22, the exterior uppermost edge of the storage means 233 has a flared portion 247 for providing an aligning function for the receiving of the apparatus 210 as it is moved in place by mechanical means. In the illustrated embodiment shown in FIG. 21, a foam core 250 may be used in the receptacle to give a more firm and secure closure by drawing the apparatus 210 into the foam core 250.

The raised inclined surfaces 232 on cylinder 217 are functionally related in at least one case to at least two pins 235 which project from the storage member 233. The raised inclined surfaces 232 are designed to be in sliding relationship with the at least two pins 235 as the cylinder 217 and dispensing container 215 are placed in proximity to the at least two pins 235 of the storage means 233. Thus, the cylinder 217 and dispensing container 215 are rotated while locked in the unit nesting configuration, the two pins 235 travel along the incline surfaces 232A until they reach the two relatively flat surfaces 232B at the upwardmost point of the inclined surface 232A for locking the apparatus 210 in a fixed position. Two stopping members 236 proximate the two relatively flat surfaces 232B for a final resting position for the storage and/or indexing of units from the apparatus 210.

Referring again to FIG. 12, a wheel member 237 is provided and is connected to a shaft 238 which is, in turn, connected to the dispensing container 215 by passing the shaft 238 and spacer 238A through the aperture 229 in the end 227 of the cylinder 217. The end effector 112 can securely mate to pins 237A, using channels 241 (and colinear channel 240 through the dispensing container 215) to guide a pin (not shown) on the end effector 112 to aid in coupling the end effector to the wheel member 237. Also located about the shaft 238 and between the wheel member 237 and the end 227 of the lower portion 220 of the cylinder 217 is the resilient member 223. The wheel member 237 has at least two projections 237A therefrom for interfacing with the end effector 112 of the robotics subsystem 40.

Upon the application of positive pressure applied axially to the wheel member 237 as represented by arrows 249 in sufficient force to overcome the resilient spring 223, the male member 221 and the female member 228 are disengaged and, upon the application of torque to the wheel member 237 as shown in FIG. 19, the cylinder 217 and dispensing container 215 are capable of being rotated independent of each other and yet still be in nesting relationship.

Thus, when the apparatus 210 is securely fastened to receptacle 88, shown in FIGS. 20 and 21, and a positive pressure is applied axially to the shaft 238 of wheel member 237 sufficient to overcome the spring 223, then cylinder 217 and container 215 can be rotated independently.

Figure 24:
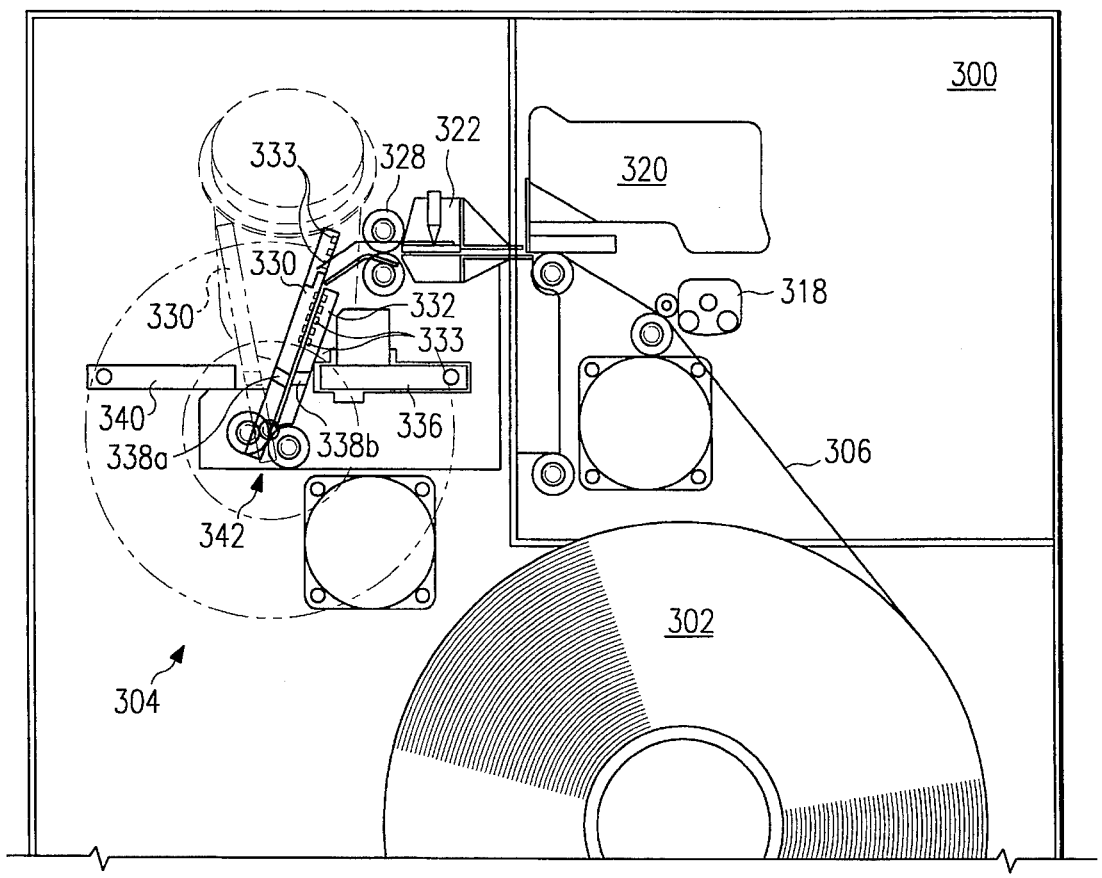
FIG. 24 illustrates a front view of the packaging subsystem.
Figure 25A:
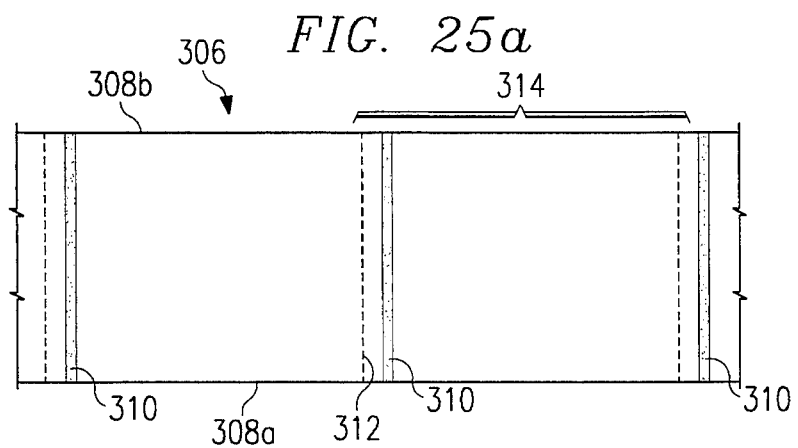
FIGS. 25a–b illustrate the preferred embodiment of the packaging material used in the packaging subsystem of FIG. 24.
Figure 25B:
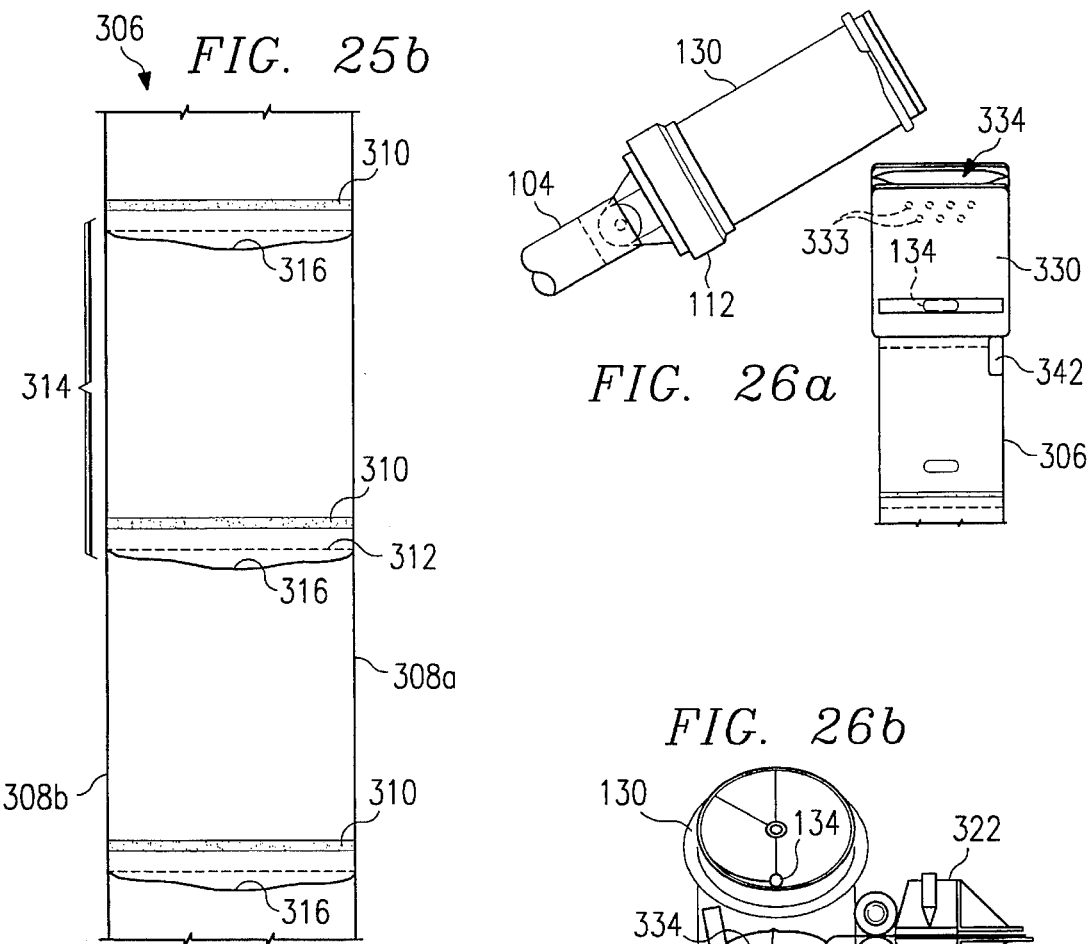
Figure 26A:
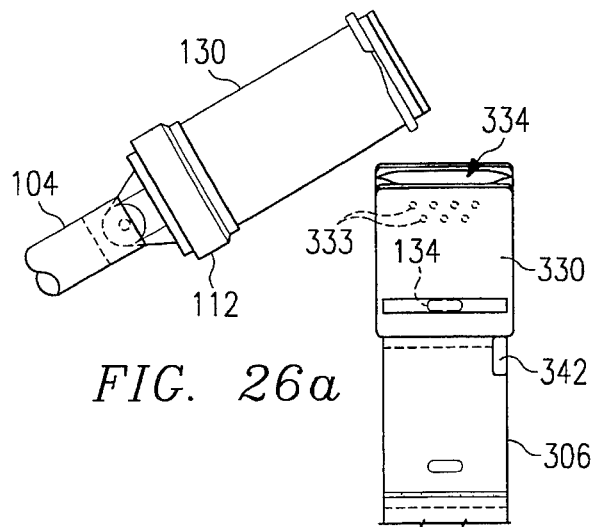
FIGS. 26a–b illustrate side and front views, relative to the container, illustrating the dispensing of a medication unit into the packaging subsystem.
Figure 26B:
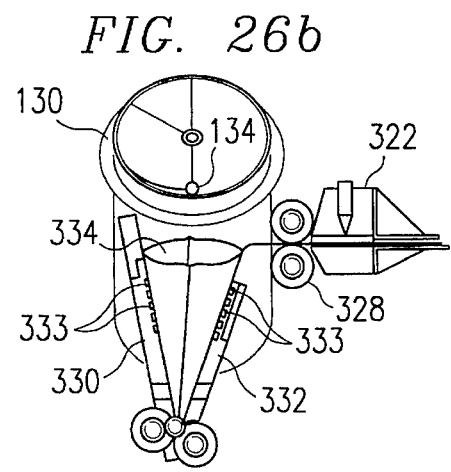

FIGS. 24–26 illustrate the medication packaging subsystem 38. The packaging subsystem comprises a printing module 300, a bulk material reel 302 and a opener/sealer 304. The bulk material reel 302 comprises a reel for dispensing a strip of packaging material, which is shown in greater detail in connection with FIGS. 25a–b. The packaging material 306 comprises a continuous strip of two-ply package material sealed on edges 308a–b. Pockets 314 of material are created by seals 310. Just below each seal 310, a perforation 312 is formed such that each pocket 314 can be easily separated from the strip. On one side of the two-ply material, the perforation is pre-opened such that the pocket 314 is accessible. This material can be purchased from a variety of manufacturers in the form described, i.e., having pre-sealed pockets 314 wherein one side of the material has a perforation 312 and the other side of the material has a slit 316 to allow access to the interior of the pocket 314. By using material which has the pre-formed pockets described above, the mechanics of the packaging subsystem 38 is simplified.

The packaging material 306 is pulled through roll-drives 318 to the printhead 320. Printheads for printing directly to a plastic material are available from a number of sources. The output from the printhead 320 is directed to cutter 322. The cutter 322 separates strips of packages for different patients. After passing cutter 322, the packaging material is directed through roll-drive 328 where a pocket 314 is disposed between first and second vacuum arms 330 and 332. Vacuum arm 330 is rotatable under control of the control electronics 36. Prior to dispensing medication from a container 90, a vacuum is applied to vacuum arms 330 and 332 through holes 333, such that the plastic material 306 is temporarily adhered to the vacuum arms. Vacuum arm 330 is rotated outward such that an opening 334 is created at the top of pocket 314 to provide the maximum clearance for the medication to be dispensed.

After the opening 334 is formed, the container 90 is rotated to drop the medication unit into the opening. A "light curtain" is directed across the width of the pocket 314 by light source 306. The light curtain travels through slits 338a–b formed in vacuum arms 330 and 332, respectively, and the light produced thereby is detected by a detector 340. The detector 340 outputs a signal indicating whether the curtain of light is broken, thereby indicating whether the pill from the container 130 (or other medication unit from container 210) has landed in the package.

After the pill is detected, the package is driven down its path by roller drive 342 and the opening 334 is closed and sealed.

By using the packaging material 306, which is perforated and slit, as shown in FIG. 25a, the mechanics of the packaging subsystem can be reduced. However, it is also possible to provide a packaging subsystem wherein the packaging material is not pre-slit and/or not pre-perforated. In this embodiment, the packaging material is sealed by the packaging subsystem 38 to begin a package, and slit to receive a medication unit. After the medication unit is placed in the pocket formed by the seal and the sides of the packaging material, another seal is formed to encapsulate the medication unit. The package can then be perforated by the packaging subsystem.

Other mechanisms can also be used to provide the opening 334 to the pocket 314 formed in the packaging material for transfer of the medication unit. One such alternative mechanism is a blower disposed above the packaging material to provide an airflow towards the slit 316. This air flow will cause air to flow into the pocket and hence separate the sheets forming the pocket. Thus, a wide opening can be achieved. While this embodiment is advantageous because it simplifies the mechanics of the packaging subsystem 38, it may be more difficult to implement due to the effect of the air flow on the medication unit as it falls into the pocket.

It is important to note that both bulk medication containers 130 and module containers 210 can be used to drop units directly into the package 314. Since the medication drops directly through the opening 334 into the pocket 314, there is no cross-contamination, i.e., medication units do not touch a surface which has been touched by a medication unit of another type. Cross-contamination is a particular problem in systems which require a funnel or ramp to guide medication into the package, since the funnel or ramp will become contaminated by each pill with which it comes in contact.

Figure 27A:
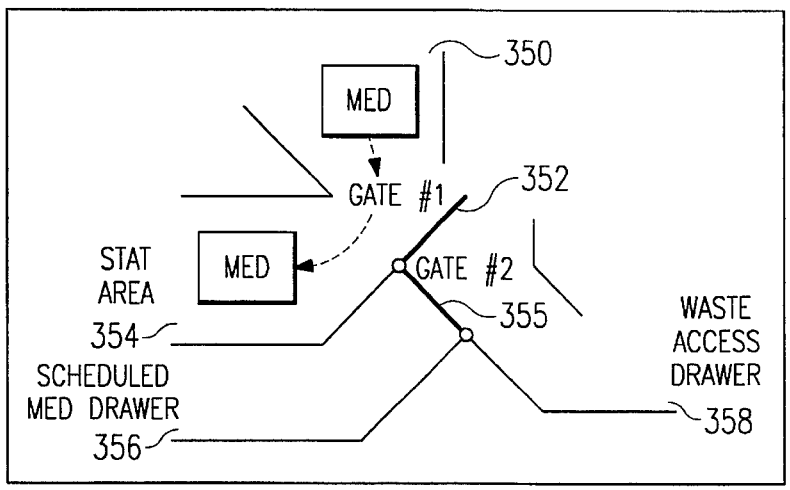
FIGS. 27a–c illustrate the gating for dispensing medication packages.
Figure 27B:
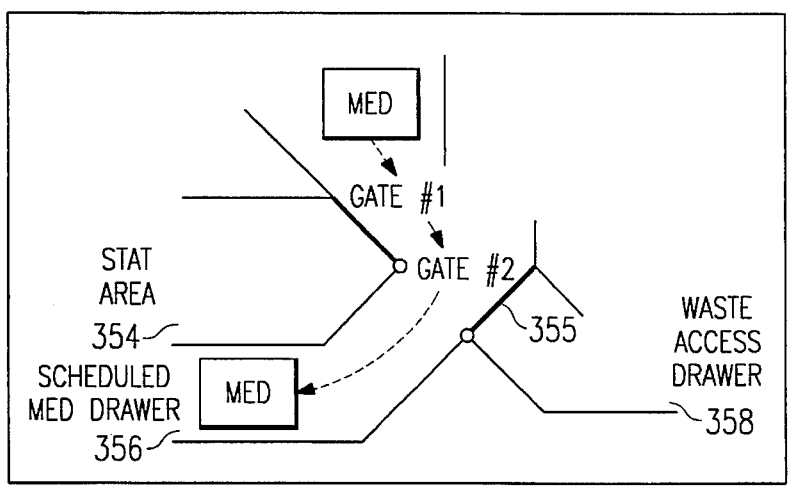
Figure 27C:
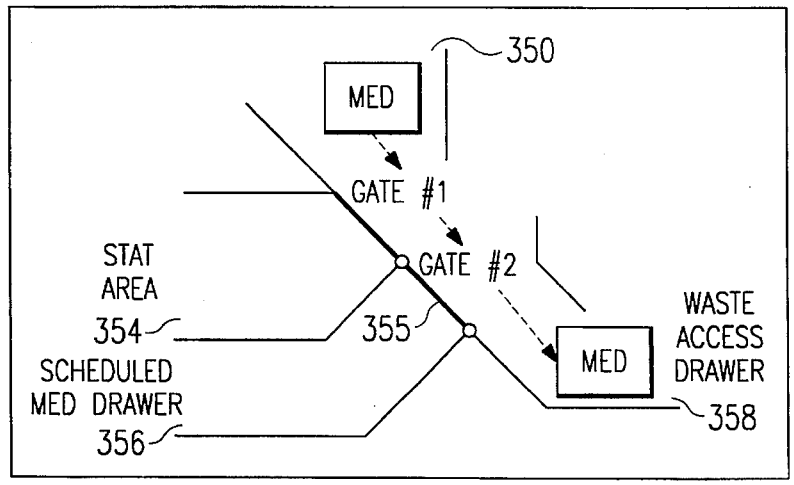

FIGS. 27a-c illustrate a gating mechanism for directing the passage between packages of medication and the exterior of the dispenser 12. All output from the packaging subsystem 38 is directed down chute 350. A gate 352 directs such packages to a stat area 354 if the nurse has requested the package to be delivered stat, i.e., while the nurse waits. Gate 352 closes and gate 355 opens to direct packages to a scheduled medication drawer 356 (see FIG. 27b). The scheduled medication drawer is the default path for the package to take. By directing the package to the scheduled medication drawer, the nurse may perform other duties while the package (or packages for a number of patients) are being prepared and the nurse can return to remove the packages from the scheduled medication drawer 356 when the packages are finished. The scheduled medication drawer can only be opened upon proper authority. FIG. 27c illustrates the path to the waste access drawer where both gate 352 and gate 355 are closed. The waste access drawer is for surplus packaging material which results from the packaging process and return of unused medications.

The present invention provides a number of advantages over the prior art. First, the system can be used with existing pharmacy software such that patient orders can be entered using existing procedures. Second, medications can be transferred from the pharmacy to the various dispensers in bulk containers, which greatly reduces the time involved in preparing medication orders. Third, the system provides security against unauthorized personnel gaining access to hospital medical supplies. Fourth, the dispensers can account for each medication removed. Fifth, the dispensers only allow removal of medication which has been authorized by a physician and entered into the pharmacy database. Sixth, each patient's package is labelled with the patient's demographic information and with information pertaining to the medication in the package to reduce administration errors. Seventh, the medication is transferred to the package without any cross-contamination between medications. Eighth, the dispensers reduce human error in providing the medication for individual patients.

Although the present invention and its advantages have been described in detail, it should be understood that various changes, substitutions and alterations can be made herein without departing from the spirit and scope of the invention as defined by the appended claims.

What is claimed is:

1. Apparatus for dispensing medication in a hospital comprising:
   a plurality of containers for holding medication units;
   a plurality of holders for holding one or more medication units from associated containers;
   an imaging system for generating an image of the medication units in a selected holder to determine whether a desired number of medication units are present;
   packaging apparatus for containing one or more medication units in a package; and
   robotics for manipulating a holder to transfer one or more medication units from the container directly to said package.

2. The apparatus of claim 1 and further comprising a storage module for holding a plurality of said containers.

3. The apparatus of claim 2 wherein said storage module comprising a rotating carousel having a plurality of receptacles disposed thereon for receiving respective containers.

4. The apparatus of claim 1 wherein each holder is coupled to an associated container.

5. The apparatus of claim 4 and further comprising control circuitry for controlling said robotics to manipulate said containers to place said desired number of medication units in the associated holder.

6. The apparatus of claim 1 wherein said packaging apparatus comprises:
   holding means for holding packaging material; and
   apparatus for opening a pocket in said packaging material into which said one or more medication units are transferred.

7. The apparatus of claim 1 and further comprising an interface to a hospital pharmacy system for retrieving data therefrom.

8. The apparatus of claim 1 and further comprising a user interface for receiving instructions from a user and issuing instructions to cause transfer of said medication units from said containers to said packaging apparatus.

9. The apparatus of claim 8 and further comprising control circuitry coupled to said user interface, said packaging apparatus and said robotics.

10. The apparatus of claim 9 and further comprising a printer coupled to said user interface for printing reports.

11. A system of dispensing medications throughout a hospital comprising:
   circuitry for maintaining a database of information associated with patient medication orders; and
   a plurality of medication dispensers for dispensing medication responsive to said database of information, each dispenser comprising:
   a plurality of containers for holding medication units;

a plurality of holders for holding one or more medication units from associated containers;

an imaging system for generating an image of the medication units in a selected holder to determine whether a desired number of medication units are present;

packaging apparatus for containing one or more medication units in a package; and robotics for manipulating a holder to transfer one or more medication units from the container directly to said package.

12. The system of claim 11 wherein each dispenser further comprises a rotating carousel having a plurality of receptacles disposed thereon for receiving respective containers.

13. The system of claim 11 wherein each holder is coupled to an associated container.

14. The apparatus of claim 13 and further comprising control circuitry for controlling said robotics to manipulate said containers to place said desired number of medication units in the associated holder.

15. The apparatus of claim 11 wherein said packaging apparatus comprises:

holding means for holding packaging material; and apparatus for opening a pocket in said packaging material into which said one or more medication units are transferred.

16. The apparatus of claim 15 wherein said apparatus for forming a pocket comprises first and second arms for applying a vacuum to respective first and second sides of the packaging material, at least one of said first and second arms being movable to displace a portion of said first side from a portion of said second side to form an opening to the pocket.

17. The apparatus of claim 11 wherein said packaging apparatus further comprises a printer for printing patient and medication administration information on said packaging material.

18. Apparatus for dispensing medication in a hospital comprising:

a plurality of containers for holding medication units, said containers having a holding area for temporarily holding one or more medication units;

packaging apparatus for containing one or more medication units in a package; and an imaging subsystem for detecting the presence of a single medication unit in said holding area;

robotics for manipulating a selected container to transfer medication unit from the container directly to said package.

19. The apparatus of claim 18 wherein said subsystem detects the absense of any medication units in said holding area.

20. The apparatus of claim 19 wherein said subsystem detects the presence of more than a single medication unit in said holding area.

21. The apparatus of claim 19 wherein said subsystem comprises imaging circuitry for generating an image of the contents of said holding area.

22. The apparatus of claim 21 wherein said subsystem further comprises processing circuitry for identifying a cusp in said image and generating a control signal in response thereto.

23. The apparatus of claim 21 wherein said subsystem further comprises processing circuitry for comparing said image with pill-specific information to determine whether a single pill is present in said holding area.

24. The apparatus of claim 23 and further comprising a database coupled to said processing circuitry for storing said pill-specific information.

25. The apparatus of claim 23 wherein said pill-specific information includes pill dimension and shape information.

26. The apparatus of claim 18 wherein said subsystem includes a plurality of imaging circuits to provide images of the holding area from different angles.

* * * * *